United States Patent [19]
Otterness et al.

[11] Patent Number: 6,030,792
[45] Date of Patent: Feb. 29, 2000

[54] ASSAYS FOR MEASUREMENT OF PROTEIN FRAGMENTS IN BIOLOGICAL MEDIA

[75] Inventors: Ivan G. Otterness, Groton; Peter S. Mezes, Old Lyme; James T. Downs, Norwich; Kimberly S. Johnson, Gales Ferry, all of Conn.

[73] Assignee: Pfizer Inc, New York, N.Y.

[21] Appl. No.: 09/184,658

[22] Filed: Nov. 2, 1998

Related U.S. Application Data

[60] Provisional application No. 60/065,423, Nov. 13, 1997.

[51] Int. Cl.$^7$ .................................................... G01N 33/53
[52] U.S. Cl. ........................... 435/7.1; 435/7.5; 435/7.7; 435/7.9; 435/975; 530/387.9; 530/388.85; 530/389.1; 530/866; 530/391.3
[58] Field of Search ............................. 435/7.1, 7.5, 7.7, 435/7.9, 7.92–7.95, 326, 331, 975, 328; 436/518, 531, 811; 530/356, 387.1, 387.9, 388.1, 388.85, 389.1, 391.1, 391.3, 866

[56] References Cited

U.S. PATENT DOCUMENTS 5,541,295  7/1996  Barrach et al. ...................... 530/388.1

OTHER PUBLICATIONS

Metsäranta et al. "Mouse Type II Collagen Gene", *The Journal of Biological Chemistry*, vol. 266, No. 25 (Sep. 5, 1991), pp. 16862–16869. QP501.J7.

Van Regenmortel *Structure of Antigens*. Florida, CRC Press, Inc, 1992. pp. 7–8. QR 186.5.S76.

*Primary Examiner*—Jeffrey Stucker
*Attorney, Agent, or Firm*—Peter C. Richardson; Gregg C. Benson; Mervin E. Brokke

[57] ABSTRACT

This invention provides novel antibodies and engineered versions thereof and methodology for monitoring biological media for protein fragments, especially collagen fragments resulting from collagenase cleavage of type II collagen.

24 Claims, No Drawings

ASSAYS FOR MEASUREMENT OF PROTEIN FRAGMENTS IN BIOLOGICAL MEDIA

This application claims the benifit of U.S. Provisional Application No. 60/065,423, filed Nov. 13, 1997.

FIELD OF THE INVENTION

This invention relates to methods for detecting protein fragments in biological media. More specifically, it relates to methods for quantitating collagen fragments resulting from collagenase cleavage of type II collagen.

BACKGROUND OF THE INVENTION

The physiological turnover of articular cartilage represents a fine balance between synthesis and degradation. It is a feature of normal growth and development and maintenance of cartilage in the adult. Net cartilage loss is a feature of rheumatoid arthritis and osteoarthritis. It is strongly associated with disability and a low quality of life. Cartilage destruction in rheumatoid arthritis and osteoarthritis is currently diagnosed based on combined clinical symptoms and radiological findings. Damage to articular cartilage occurs early in the disease, long before it can be detected radiologically; damage is detected radiologically only after there is extensive and probably irreversible cartilage loss. Therefore, it is of critical importance that clinicians have biochemical markers for early diagnosis of cartilage damage so therapy can be initiated early, before extensive damage is done.

Type II collagen constitutes the bulk of the fibrillar backbone of the cartilage matrix, just as type I collagen forms the fibrillar organization of the extracellular matrix of most other tissues such as skin, bone, ligaments and tendons. These collagens are composed of a tightly wound triple helix, which can only be cleaved by metalloproteinase collagenases to produce ¾ and ¼ length α-chain fragments that are identifiable by polyacrylamide gel electrophoresis.

The destruction of articular cartilage during arthritic disease is due, in part, to the degradation of the extracellular matrix, which is composed primarily of fibrillar type II collagen and aggregating proteoglycans. In articular cartilage, type II collagen fibrils are responsible for the tensile strength whereas the proteoglycans provide the compressive stiffness necessary for normal articulation and function. The precise mechanisms by which these connective tissue components are degraded are not fully understood. In mammals, an important mechanism involves the collagenases which are a group of enzymes capable of site-specific cleavage of helical (native) collagen.

SUMMARY OF THE INVENTION

This invention comprises a method for monitoring biological media for protein fragments, preferably, collagen fragments, said fragments resulting from collagenase cleavage of type II collagen which comprises; contacting said biological media with a capture antibody; said capture antibody being active against the sequences set forth in the Sequence Listing as SEQ ID NOS: 1 and 2; and in a second step, contacting said biological media with a detection antibody; said detection antibody being active against the sequences set forth in the Sequence Listing as SEQ ID NOS: 3 and 4; and finally, detecting the amount of collagen fragments bound to said capture and detection antibodies using standard techniques which are well known to those with ordinary skill in this art.

Those skilled in this art will recognize that the order of contacting the antibodies with the biological media may be reversed.

Therefore, in another aspect, this invention comprises a method for monitoring biological media for protein fragments which comprises;
  detecting the amount of collagen fragments bound to said capture and detection antibodies; or
  contacting said biological media with a capture antibody; said capture antibody being active against the sequences set forth in the Sequence Listing as SEQ ID NOS: 3 and 4; and
  contacting said biological media with a detection antibody; said detection antibody being active against the sequences set forth in the Sequence Listing as SEQ ID NOS: 1 and 2; and
  detecting the amount of collagen fragments bound to said capture and detection antibodies.

In a preferred aspect, this invention provides a method for the detection of protein fragments which are collagen fragments generated by collagenase cleavage of articular cartilage and more particularly, a method wherein said protein fragments are generated from collagenase cleavage of type II collagen.

In yet another aspect, this invention provides a third method for monitoring biological media for collagen fragments generated from articular cartilage which comprises;
  contacting said biological media with an antibody active against the sequences set forth in the Sequence Listing as SEQ ID NOS: 3 and 4; and
  detecting the amount of collagen fragments bound to said antibody.

In a broader aspect this invention provides a method for monitoring biological media for protein fragments which comprises;
  contacting said biological media with an antibody capable of recognizing and binding to protein fragments containing the sequences set forth in the Sequence Listing as SEQ ID NOS: 3 and 4; and
  detecting the amount of protein fragments bound to said antibody.

This invention provides a capture antibody which is a monoclonal antibody.

This invention also provides a detection antibody which is a monoclonal antibody.

This invention provides a monoclonal antibody, designated 9A4, which has the $V_H$ sequence set forth in the Sequence Listing as SEQ ID NO: 5 and the $V_L$ sequence set forth in the Sequence Listing as SEQ ID NO: 6.

This invention provides an antibody which is a genetically engineered antibody, and is related, but not necessarily identical in sequence to scFv 9A4 of p9A4ICAT7-1 (ATCC 98593), ATCC, American Type Culture Collection, 10801 University Blvd., Manassas, Va. 20110–2209 USA, and p9A4IF-5 (ATCC 98592), which correspond to SEQ ID NOS: 7 and 8 set forth in the Sequence Listing, respectively.

This invention provides an antibody which is a genetically engineered antibody, and is related, but not necessarily identical in sequence to scFv 5109 of p5109CscFv7 (ATCC 98594), and as set forth in the Sequence Listing as SEQ ID NO: 9.

This invention provides a monoclonal antibody, designated 5109, which has the $V_H$ sequence set forth in the Sequence Listing as SEQ ID NO: 10 and the $V_L$ sequence set forth in the Sequence Listing as SEQ ID NO: 11.

This invention provides a method for detecting protein fragments employing an antibody, designated 5109, and which has the $V_H$ sequence set forth in the Sequence Listing as SEQ ID NO: 10 and the $V_L$ sequence set forth in the Sequence Listing as SEQ ID NO: 11.

In another aspect, this invention provides a hybridoma cell line that produces a monoclonal antibody that binds to peptides consisting essentially of the structure as set forth in the Sequence Listing as SEQ ID NO: 1 or SEQ ID NO: 2, the cell line having the identifying characteristics of ATCC HB-12436.

In another aspect, this invention provides a hybridoma cell line that produces a monoclonal antibody that binds to peptides consisting essentially of the structure as set forth in the Sequence Listing as SEQ ID NOS: 3 or 4, the cell line having the identifying characteristics of ATCC HB-12435.

In still another aspect, this invention provides an *E. coli* culture which produces a genetically engineered antibody related to 9A4 that binds to peptides consisting essentially of the structure set forth in the Sequence Listing as SEQ ID NOS: 1 or 2.

In another aspect, this invention provides an *E. coli* culture which produces a genetically engineered antibody related to 5109 that binds to peptides consisting essentially of the structure set forth in the Sequence Listing as SEQ ID NOS: 3 or 4.

In yet another aspect, this invention provides a bispecific antibody produced by hybridization of the antibodies 9A4 and 5109 wherein each half antibody recognizes its respective binding partner.

In another aspect, this invention provides a bispecific antibody which is a genetically engineered combination of antibodies 9A4 and 5109 produced by combining the $V_L$ and $V_H$ domains of the two antibodies in the form $V_L(5109)$-linker-$V_H(5109)$-linker-$V_L(9A4)$-linker-$V_H(9A4)$ and equivalents thereof.

This invention further provides a method for monitoring collagen fragments in biological media which comprises: contacting said biological media with a bispecific antibody 9A4/5109 described above; and detecting the amount of collagen fragments bound to said antibody.

This invention also provides a bispecific antibody produced from genetically modified variants of antibodies 5109 and 9A4.

DETAILED DESCRIPTION OF THE INVENTION

Type II collagen is the structural protein that gives articular cartilage its tensile strength and shear resistance. It also provides the stuctural basis for the containment of proteoglycan that imparts compressive resistance and in doing so directly determines the form of the osmotically pressurized cartilage. Thus the structural integrity of type II collagen is a major determinant of the physical properties and the durability of articular cartilage.

The progressive failure of articular cartilage is one of the hallmarks of arthritic disease. Where that failure is based on changes in the type II collagen structure, it would be advantageous to have methodology to measure specificially the breakdown of type II collagen. Fragments of type II collagen from articular cartilage are released into the synovial fluid, lymph, blood and urine as type II collagen breaks down. Measurement of surviving fragments would provide a method for monitoring type II collagen breakdown to detect the onset of arthritic disease and measure disease progression. Moreover, it would also be useful to measure the effect of therapy on type II collagen breakdown during disease.

A variety of methods have been utilized to monitor collagen breakdown. In mammalian tissues, collagenase appears to be the rate-limiting extracellular enzyme involved in breakdown of type II collagen (1). Collagenase fragmentation of collagen into a three quarters and one quarter piece was identified as early as 1967 (2,3) and there are currently three identified mammalian collagenases involved in breakdown of type II collagen (4,5). Other enzymes are involved in further fragmentation of type II collagen. Lysosomal breakdown of the fibrillar collagens is known in bone and liver (6,7). Since collagen is one of the few proteins characterized by a high hydroxyproline content, measurement of urinary hydroxyproline has been examined as a measure of collagen turnover (8). However, since type I and type III collagens are found in large amounts in skin, bone, and connective tissues in general, the method has not been found useful for measuring breakdown of either a particular type of collagen or of collagen from a particular body compartment, e.g., bone, and is of no value for monitoring type II collagen since it provides only an extremely small portion of the daily urinary secretion of hydroxyproline (8). Therefore efforts to monitor breakdown of collagen or collagen itself have focused on immunological methods.

Antibodies can discriminate collagen fragments unique to a collagen type and cleavage site and potentially monitor the specific mode of collagen breakdown (9). Polyclonal and monoclonal antibodies have been prepared against type I and III collagen or their fragments; and assays have been prepared for the collagen breakdown products of type I and type III collagens, for example, see Eyre (10). Relatively few methods have been reported to develop antibodies against breakdown products of type II collagen.

Polyclonal and monoclonal antibodies have been prepared against type II collagen (9,11–13). These antibodies have been utilized for the detection of intact type II collagen rather than the quantitative determination of collagen fragments. Eyre, however, (14) has prepared monoclonal antibodies against type II collagen fragments containing the crosslinking residues. He developed an assay for breakdown of type II collagen based on the crosslink fragment containing a type II collagen specific sequence similar to his issued patent (10). Dodge and Poole prepared polyclonal antibodies against denatured type II collagen that were unreactive with other collagens (15,16). The epitope was sequenced and later Hollander and Poole (17,18,19,) prepared a competitive antibody assay against the type II collagen fragments having the sequences set forth in the Sequence Listing as SEQ ID NOS: 12 and 13 using a monoclonal antibody. Hollander and Croucher (20) also made a capture Elisa using antibodies directed against peptides outlined in the Sequence Listing as SEQ ID NO: 67, 68 or 69. Billinghurst et al. (21) have prepared polyclonal antibody against the collagen cleavage site neoepitope of type II collagen (having the sequence set forth in the Sequence Listing as SEQ ID NO: 2) and have prepared a competitive type II collagen assay. Srinivas, Barrach, and Chichester (22–24) have prepared multiple monoclonal antibodies for a type II collagen assay using the cyanogen bromide fragments of type II collagen as antigen. Although the epitopes reactive with the antibody have not been identified (25), they too are able to assay type II collagen.

Capture Elisa's are a reliable method for obtaining high specificity since it is based on two antibodies coordinately recognizing two different amino acid clusters in the same molecule. As the antibody binding site contains as few as six amino acids, sequences as small as 15 to 20 amino acids can be recognized by two antibodies in a capture assay. Competitive assays use a single antibody and thus allow measurement of polypeptides as small as 6–8 amino acids, but they lack the specificity of the dual antibody measurement. In addition, competitive assays lack the sensitivity of capture Elisa's which often have a 100–10,000 times lower limit of detection. Thus capture Elisa's provide a preferred method for measuring metabolic fragments of proteins. For example, a capture Elisa has been used to measure breakdown fragments of the structural protein elastin in blood (26). A capture Elisa has been used to measure the 21 amino acid biologically active peptide endothelin (27). A pair of capture Elisa's have been used to measure different metabolic fragments of the 28 amino acid glucagon peptide (28). Based on such results, a minimal 22 amino acid peptide fragment was selected that could be used to construct a capture Elisa to measure collagenase dependent metabolism of type II collagen.

This invention provides two types of assays of type II collagen metabolism. Both assays are based on an antibody (polyclonal, monoclonal or genetically engineered antibody) against a defined sequence of type II collagen against which antibodies have not been previously prepared. The sequence is rich in acidic residues, i.e., the sequence set forth in the Sequence Listing as SEQ ID NO: 3 from which a deletion has been made at the C-terminus by 1 residue. As no mammalian extracellular aspartyl or glutamyl endopeptidases have been described, collagen fragments rich in acidic residues should survive further metabolism and be available for measurement in body fluids. Antibody against those residues or a collagen fragment containing those residues would provide a general method of detection of type II fragments in body fluids independent of the method of generation of the collagen metabolite. This invention provides monoclonal antibody 5109 and genetically engineered variants of 5109 that are specific for the type II collagen sequence and bind to collagen fragments containing the sequence.

The first assay is a general method for assessing the breakdown of type II collagen. This assay provides a general competitive method for quantitating the amount of the sequence set forth in the Sequence Listing as SEQ ID NO: 3 from which a deletion has been made at the C-terminus by 1 residue, and its closely related congeners.

For the second assay, an additional antibody was made against the sequence set forth in the Sequence Listing as SEQ ID NO: 14. There is a free C-terminal carboxyl group on the glycine (residue 9 of SEQ ID NO: 14). This sequence is obtained when collagenase cleaves type II collagen and therefore it is classified as a neoepitope, i.e., it is not present in the native sequence (the sequence set forth in the Sequence Listing as SEQ ID NO: 15, continues -GPOGPQG/LAG-where collagenase cleaves at the vertical bar), but arises when collagen is cleaved by collagenase. Polyclonal antibodies against that sequence have been previously reported (22). Monoclonal antibody 9A4 and genetically engineered derivatives therefrom react with the neoepitope sequence set forth in the Sequence Listing as SEQ ID NO: 2, but fail to react with uncleaved type II collagen or type I collagen. While the neoepitope sequence is unique to type II collagen when cleaved by collagenase, a homologous and weakly cross-reactive sequence is generated in type I collagen when cleaved by collagenase (SEQ ID NO: 16 as set forth in the Sequence Listing). This is also true for type III collagen; it generates the weakly cross-reactive sequence set forth in the Sequence Listing as SEQ ID NO: 2, when cleaved by collagenase. Thus the neoepitope antibody lacks full specificity for type II collagen and would fail to selectively detect cleavage of type II collagen by collagenase if used alone. However, when antibody 5109 and antibody 9A4 are combined in a sandwich assay the two antibodies together can selectively detect type II collagen metabolites generated by collagenase. Moreover, an advantage that the sandwich type of assay provides in this invention is a 100 fold lower limit of detection compared to a simple competitive assay based on 9A4 alone. The sandwich assay format with the antibodies described in this invention thus provides a unique method for monitoring type II collagen metabolism by collagenase in normal and pathological conditions, which has not been previously described.

Alone, antibody 9A4 is a novel monoclonal antibody that has use for the detection of collagenase cleaved fragments of type I or type II or type III collagen, so long as it is not necessary to distinguish the collagen type.

REFERENCES

1. Harris E D, Jr, Krane S. Collagenases, N Engl J Med 1974; 291:557–563, 605–609, 652–661.

2. Nagai Y, Lapiere C M, Gross J. Tadpole collagenase. Preparation and purification. Biochemistry 1966;5:3123–3130.

3. Sakai T, Gross J. Some properties of the products of reaction of tadpole collagenase with collagen. Biochemistry 1967;6:518–528.

4. Pendas A M, Matilla T, Estivill X, Lopez-Otin C. The human collagenase-3 (CLG3) gene is located on chromosome 11q22.3 clustered to other members of the matrix metalloproteinase gene family. Genomics 1995;26:615–8.

5. Mitchell P G, Magna H A, Reeves L M, Lopresti-Morrow L L, Yocum S A, Rosner P J, Geoghegan K F, Hambor J E. Cloning, expression, and type II collagenolytic activity of matrix metalloproteinase-13 from human osteoarthritic cartilage. J Clin Invest 1996;97:761–8.

6. Maciewicz R A, Wotton S F, Etherington D J, Duance V C. Susceptibility of the cartilage collagens type II, IX and XI to degradation by the cysteine proteinases, cathepsins B and L. FEBS Lett 1990;269:189–193.

7. van Noorden C J F, Everts V. Selective inhibition of cysteine proteinases by z-phe-alaCH$_2$F suppresses digestion of collagen by fibroblasts and osteoclasts. Biochem Biophys Res Comm 1991;178:178–184.

8Kivirikko, K. I. Urinary secretion of hydroxy-proline in health and disease. Int. Rev. Connect Tissue Res. 1970; 5, 93–163.

9. Timpl R. Antibodies to collagens and procollagen. Methods Enzymol 1982;82:472498.

10. Eyre D. Patent. U.S. Pat. No. 5,320,970.

11. Holmdahl R, Andersson M, Tarkowski A. Origin of the autoreactive anti-type II collagen response. I. Frequency of specific and multispecific B-cells in primed murine lymph nodes. Immunology 1987;61:369–374.

12. Punjabi C J, Wood D D, Wooley P H. A monoclonal anti-type II collagen antibody with cross reactive anti-Ig activity specific for the F(ab')$_2$ fragment. J Immunol 1988;141:3819–3822.

13. Jasin H E, Taurog J D. Mechanisms of disruption of the articular cartilage surface in inflammation. Neutrophil elastase increases availability of collagen II epitopes for binding with antibodies on the surface of articular cartilage. J Clin Invest 1991;87:1531–1536.

14. Norlund L L, Shao P, Yoshihara P, Eyre D R. Markers of bone type I and cartilage type II collagen degradation in the Hartley guinea pig model of osteoarthritis. Trans Orthoped Res Assoc 1997;22:313.

15. Dodge G R, Poole A R. Immunohistochemical detection and immunochemical analysis of type II collagen degradation in human normal, rheumatoid and osteoarthritic articular cartilages and in explants of bovine articular cartilage cultured with interleukin-1. J Clin Invest 1989;83:647-661.

16. Dodge G R, Pidoux I, Poole A R. The degradation of type II collagen in rheumatoid arthritis: an immunoelectron microscopic study. Matrix 1991;1 1:330–338.

17. Poole A R. WO 94/14070.

18. Hollander A P, Heathfield T F, Webber C, Iwata Y, Bourne R, Rorabeck C, Poole A R. Increased damage to type II collagen in osteoarthritic articular cartilage detected by a new immunoassay. J Clin Invest 1994;93:1722–32.

19. Hollander A P, Pidoux I, Reiner A, Rorabeck C, Bourne R, Poole A R. Damage to type II collagen in aging and osteoarthritis starts at the articular surface, originates around chondrocytes, and extends into the cartilage with progressive degeneration. J Clin Invest 1995;96:2859–69.

20. Hollander A P, Croucher L J. Assay for collagen type II fragments. WO 98/3523520.

21. Billinghurst R C, Dahlberg L, Ionescu M, Reiner A, Bourne R, Rorabeck C, Mitchell P, Hambor J, Diekmann O, Tsechesche H, Chen J, van Wart H, Poole A R. Enhanced cleavage of type II collagen by collagenases in osteoarthritic articular cartilage. J Clin Invest 1997;99:1534–1545.

22. Srinivas G R, Barrach H J, Chichester C O. Quantitative immunoassays for type II collagen and its cyanogen bromide peptides. J Immunol Meth 1993;159:53–62.

23. Srinivas G R, Chichester C O, Barrach H J, Matoney A L. Effects of certain antiarthritic agents on the synthesis of type II collagen and glycosaminoglycans in rat chondrosarcoma cultures. Agents Actions 1994;41:193–199.

24. Srinivas G R, Chichester C O, Barrach H J, Pillai V, Matoney A L. Production of type II collagen specific monoclonal antibodies. Immunol Invest 1994;23:85–98.

25. Chichester C O, Barrach H J, Srinivas G R, Mitchell P. Immunological detection of type II collagen degradation: use in the evaluation of anti-arthritic therapies. Pharm Pharmacol 1996;48:694–698.

26. Baydanoff S, Nicoloff G, Alexiev C. Age-related changes in the level of circulating elastin-derived peptides in serum from normal and atherosclerotic subjects. Atherosclerosis 1987; 66,163–168.

27. Hamaoki M, Kato, H, Sugi M, Fujimoto M, Kurihara H, Yosizumi M, Yanagisawa M, Kimura S, Masaiki T, Yazaki Y. Monoclonal antibodies to endothelin: application for sandwich immunoassays. Hybridoma 1990; 9, 63–69.

28. Knudsen L B, Pridal L. Glucagon-like peptide-1 (9–36) amide is a major metabolite of glucagon-like peptide-1-(7–36) amide after in vivo administration to dogs, and it acts as an antagonist on the pancreatic receptor. Eur J Pharmacol 1996; 318,429–435.

DEFINITIONS

Immunoalobulin (Ig)

A natural tetrameric protein composed of two light chains of circa 23 kD and two heavy chains of circa 53–70 kD depending on the amino acid sequence and degree of glycosylation. Multimers of the tetrameric protein are also formed (IgM and IgA). There are two classes of light chains, kappa (κ) and lambda (λ), and several classes of heavy chains gamma (γ), mu (μ), alpha (α), delta (δ) and epsilon (ε). There are also subclasses. Each chain, whether a light chain or heavy chain, is made up of two parts. The first part, beginning from the N-terminus of either chain, is called the variable domain. The C-terminal half of the light chain is called the constant region of the light chain and it is the primary determinant whether the light chain is a κ or λ type. The constant region of the heavy chain comprise circa the C-terminal three-fourths of the heavy chain and determines the class of the immunoglobulin molecule ($IgG_1$, IgM, etc), i.e. a X heavy chain corresponds to an IgG and a μ heavy chain corresponds to an IgM, ect.

$V_L$ and $V_H$

The amino acid sequence of the variable domain of the light chain ($V_L$) and the variable domain of the heavy chain ($V_H$) together determine the binding specificity and the binding (kD) constant of the immunoglobulin molecule. The variable domain comprises circa half the length of the light chain and circa a quarter of the length of the heavy chain and for both chains, begins at the N-terminus of the chain. The variable regions each contain three (3) hypervariable segments known as the complementarity determining regions or CDRs.

CDR and FR

Each variable domain, $V_L$ or $V_H$, is comprised of three CDRs: CDR1, CDR2 and CDR3. The intervening sequence segments before, between and after the CDRs are known as framework segments (FR). Each $V_L$ and $V_H$ is comprised of four FR segments FR1, FR2, FR3 and FR4.

$V_\kappa$ and $V_\lambda$

The $V_L$ domain is either κ or λ, depending on which constant region ($C_\kappa$ or $C_\lambda$) is used during the productive rearrangement of the light chain ($VJC_\kappa$ or $VJC_\lambda$).

Antibody

Antibodies are specific immunoglobulin molecules produced by B-cells of the immune system in response to challenges by proteins, glycoproteins, virus cells, chemicals coupled to carriers, and other substances. An antibody is simply an immunoglobulin molecule for which its binding partner is known. The substance to which the antibody binds is called an antigen. The binding of such antibodies to its antigen is highly refined and the multitude of specificities capable of being generated by changes in amino acid sequence in the variable domains of the heavy and light chains is remarkable.

Polyclonal antibody

Normal immunization leads to a wide variety of antibodies against the same antigen. Although each B lymphocyte normally produces one immunoglobulin molecule of a defined amino acid sequence, in an immune response, many B lymphocytes are stimulated to make immunoglobulin molecules that react with the antigen, i.e., antibodies. These different antibodies are characterized by different amino acid sequences in the variable regions of the immunoglobulin molecule which result in differences in the fine specificity and affinity of binding. Such antibodies are called polyclonal antibodies to emphasize the variety of binding specificities and binding constants which arise from the variety of amino acid sequences found in the different immunoglobulin molecules utilized in the immune response.

Monoclonal Antibody (MAb)

A B lymphocyte producing a single antibody molecule can be hybridized with an immortal B lymphocyte cell line, i.e., a myeloma, to derive an antibody producing immortal cell line, i.e., a hybridoma. The hybrids thus formed are segregated into single genetic strains by selection, dilution, subdoning, and regrowth, and each strain thus represents a single genetic line. It produces a single antibody of a unique sequence. The antibody produced by such a cell line is called "monoclonal antibody" or MAb, referencing its pure genetic parentage and differentiating it from polyclonal antibody, produced from a mixed genetic background, i.e., multiple B cells. Because a MAb is a pure chemical reagent it gives consistent, uniform results in immune tests. Moreover, because the MAb is produced by an immortal cell line, reagent supply is not limiting. For these reasons, a MAb is much preferred over polyclonal antibodies for diagnostic purposes.

Genetically Engineered Antibody

As the binding specificity of an antibody resides in the variable regions of the light and heavy chains, antibodies can be genetically engineered to change or remove the constant regions and, if done properly, it can result in an antibody molecule with different properties and molecular weight, but with the same or very similar antigen binding properties. For example, the $V_L$ and $V_H$ genes can be cloned and assembled (or $V_H$ and $V_L$) with an appropriate linker between them. Such a new genetically engineered molecule is called a single chain antibody (abbreviated scFv) and typically has a molecular weight of 25–28 kD depending on the design of the linker and the addition of other sequences to help in purification, stability, trafficking, detection, etc. Multimers of the single chain antibody can also be made by appropriate use of linkers in which the order of each $V_H$, $V_L$ pair may vary. In addition, some changes in the amino acid sequence of the $V_L$ and $V_H$ region can be made that retain desirable antigen binding properties. It can be seen that an infinite variety of genetically engineered antibodies can be derived from the original antibody sequence which retain binding specificity to the antigen, but which are tailored to fulfill specific requirements. Other examples of genetically engineered antibodies include, but are not limited to: Fab, $F(ab')_2$, chimeric antibodies, humanized antibodies, etc. For a review, see Winter G and Milstein C, "Man-made Antibodies", Nature 1991; 349, 243–299.

Bispecific Antibody

Normally an IgG antibody has two identical light chains and heavy chains. There are therefore two identical antibody binding sites in the immunoglobulin molecule. By contrast, a bispecific antibody is a single immunoglobulin molecule which has two specificities. It can be made by fusion of two monoclonal antibody producing hybridoma cell lines, where each hybridoma has a different antigen specificity, and selection for a cell line (a quadroma) that produces an antibody whose composition is a tetramer composed of one light chain and one heavy chain from each hybridoma fusion partner. The antibody produced by the quadroma has only one light and one heavy chain of each parental specificity and has one binding site for each heavy/light chain pair and is bispecific, i.e., it has two binding sites of different specificities. A bispecific antibody can also be made by genetic engineering. It can comprise the $V_L$ linker $V_H$ of one antibody linked through an additional linker to a $V_L$ linker $V_H$ of another antibody molecule. The order of $V_L$ and $V_H$ can be altered, but the end result is a bispecific antibody.

Epitope

Depending on the size, structure and conformation of the antigen, an antibody may bind only to a small part of the entire structure. The part of the antigen molecule to which the antibody binds is called its epitope. Different antibodies may be mapped to different epitopes on the same antigen.

Neoecitope

The antigen may have an epitope which is hidden so that it cannot bind to a specific antibody. However, a conformational change in the antigen may cause the appearance of the epitope by unfolding or uncovering part of the surface of the molecule. This now allows the antibody to bind to the epitope. In another aspect, the action of an enzyme on the antigen may cause the appearance of a new epitope to which the antibody can bind. For example, after cleavage by a proteolytic enzyme, new N-terminal and new C-terminal sequences are generated. Because the epitope is not observed in the parent molecule and because, after some change in the parent molecule, the epitope is revealed and now can bind antibody, it is called a neoepitope.

Biological Media

This may be defined as any biological fluid that might contain the antigen and be of interest to assay by this procedure. These include: blood, synovial fluid, urine, spinal fluid, bronchiolar lavage fluid, lymph, the vitreous humor of the eye, extracts of tissues, tissue culture supernatants, extracts of cartilage, etc., Biological media need not be limited to human samples, but may also be obtained from a similar variety of animal media (mouse, rat, hamster, guinea pig, dog and bovine have been tested) in a fashion similar to the examples above.

Immunoassay

An assay for a substance (complex biological such as a protein or a simple chemical) based on using the binding properties of antibody to recognize the substance which may be a specific molecule or set of homologous molecules. The assay may involve one or more antibodies.

Direct Assay

The antibody binds directly to an antigen such as in a biological specimen (cells, tissues, histological section, etc.) or to antigen adsorbed or chemically coupled to a solid surface. The antibody itself is usually labeled to enable the determination of the amount of antibody bound to the antigen. Alternatively, the antibody (now termed primary antibody) is detected with a secondary labeled antibody that will demonstrate that binding of the primary antibody had occurred.

Competitive Assay

An assay based on the binding properties of a single antibody molecule. Typically, a labeled antigen is used to compete with an unknown antigen and the amount of unknown antigen is determined in terms of how much of the labeled antigen is displaced by the unknown antigen. The label may be radioactive, optical, enzymatic, florescent polarizing, florescent quenching, or other label. The antibody may be monospecific or bispecific.

Sandwich Assay

This is a double antibody assay in which both antibodies bind to the antigen, forming a trimeric immune complex or sandwich containing the two antibodies with the antigen between them. One antibody is utilized to localize the immune complex to the detection surface or chamber. This antibody is termed the capture antibody. The other antibody bears a label that will allow the immune complex to be detected. It is called the detection antibody. If an immune complex is not formed (no antigen is present), then the capture antibody is unable to bring the detection antibody to the detector. If antigen is present, then an immune complex will form and the capture antibody will be joined with the detection antibody such that the amount of detection antibody in the immune complex is quantitatively related to the amount of antigen present.

The assay can be formatted in many ways. For example, the capture antibody can be chemically coupled to a solid surface, or non-specifically adsorbed to a surface, attached via biotinylation to an avidin-like molecule, eg. avidin, streptavidin, neutravidin, etc., streptavidin or avidin-coated surface, coupled to magnetic particles or beads as a means of localizing the immune complex to the measurement device.

The detection antibody may be radiolabeled, or it may have a variety of possible enzymatic amplification systems such as horse radish peroxidase (HRP), alkaline phosphatase (AP), urease, etc., when formatted as an Elisa (Enzyme-linked immune assay). It may have an electrochemical, an optical, a fluorescent or other detection method to determine the amount of detection antibody in the immune complexes.

It may immediately be seen that many examples can be derived in which the two antibodies are paired in a sandwich assay using a variety of methods to capture the immune complex in a detection device and a variety of detection systems to measure the amount of immune complex.

Molecular Biology Techniques

Because the nucleotide sequences of $V_H$ and $V_L$-encoding regions are now provided for the antibodies of the present invention, a skilled artisan could in vitro produce a complete gene coding for the $V_H$ and $V_L$ regions and a completely functional antibody. It can be produced as an immunoglobulin molecule of any given class with constant regions of the heavy chain and light chain added or it can be produced as a scFv with $V_H$ and $V_L$ joined by a linker with tags added as appropriate. The constructed gene may be engineered by conventional recombinant techniques, for example, to provide a gene insert in a plasmid capable of expression. Thereafter, the plasmids may be expressed in host cells where the host cells may be bacteria such as *E. coli* or a Bacillus species, yeast cells such as *Pichia pastoris* or in mammalian cell lines such as Sp2/0, Ag8 or CHO cells.

Abbreviations

Nucleic acids, amino acids, peptides, protective groups, active groups and similar moieties, when abbreviated are abbreviated according to the IUPACIUB (Commission on Biological Nomenclature) or the practice in the fields concerned.

The following are examples.

| Standard Abbreviations | |
|---|---|
| HPLC | High pressure liquid chromatography |
| SDS-PAGE | Sodium dodecylsulfate polyacrylamide gel electrophoresis |
| PCR | Polymerase chain reaction |
| Oligo | Oligonucleotide |
| RT | Room temperature, circa 22° C. |
| Reagents: | |
| EDTA | Ethylenediamine tetraacetic acid |
| SDS | Sodium dodecylsulfate |
| TW-20 | Tween-20 |
| NFDM | Non-fat dry milk |
| DPBS | Dulbecco's phosphate buffered saline |
| Bt | Biotinylated |
| HAT | Hypoxanthine, aminopterin, thymidine containing media |
| HT | Hypoxanthine, thymidine containing media |
| HRP | Horseradish peroxidase |
| Immunoglobulin-like molecules or chains | |
| $V_H$ or $V_H$ | Variable region of the heavy chain |
| $V_L$ or $V_L$ | Variable region of the light chain |
| scFv | Single chain antibody containing a $V_L$ and $V_H$ |
| Nucleic Acids | |
| RNA | Ribonucleic acid |
| DNA | Deoxyribonucleic acid |
| cDNA | Complimentary DNA |
| mRNA | Messenger RNA |

| Nucleic acid bases | |
|---|---|
| Purines | Pyrimidines |
| A: Adenine | T: Thymine |
| G: Guanine | C: Cytosine |
| | U: Uracil |

Amino Acids-Single letter codes: Three letter codes: Full names.

| | | | | | |
|---|---|---|---|---|---|
| G: | Gly: glycine | V: | Val: valine | L: | Leu: leucine |
| A: | Ala: alanine | I: | Ile: isoleucine | S: | Ser: serine |
| D: | Asp: aspartic acid | K: | Lys: lysine | R: | Arg: arginine |
| H: | His: histidine | F: | Phe: phenylalanine | Y: | Tyr: tyrosine |

-continued

| | | | | | |
|---|---|---|---|---|---|
| T: | Thr: threonine | C: | Cys: cysteine | M: | Met: methionine |
| E: | Glu: glutamic acid | W: | Trp: tryptophan | P: | Pro: proline |
| O: | Hyp: hydroxyproline | N: | Asn: asparagine | Q: | Gln: glutamine |

EXAMPLE 1

Generation and Characterization of Monoclonal Antibody 9A4.

Balb/c mice (Jackson Laboratories, Bar Harbor, Me.) were immunized initially with the peptide having the sequence set forth in the Sequence Listing as SEQ ID NO: 17 (Anaspec, San Jose, Calif.) covalently linked to the KLH maleimide (Pierce Chemical, Rockford, Ill.) and administered in complete Freund's adjuvant (DIFCO Detroit, Mich.). The mice were boosted monthly for about 5 months using incomplete Freund's adjuvant (DIFCO, Detroit, Mich.) until the titers were 1:100,000. Mice were boosted i.v. 10 days prior to fusion. Splenocytes were collected and fused with a non-Ig secreting cell-line derived from P3X63Ag8.653 (American Type Culture Collection ATCC, Bethesda, Md.) using 50% PEG-1450 (ATCC). They were plated at $10^6$ cells/well in 96 well microtiter plates in HAT media (Sigma, St. Louis, Mo.) with 15% fetal calf serum (Hyclone, Provo, Utah). Ten days later the wells were screened by a primary Elisa. For identification of positive antibody producing wells, 10 ng/mL biotinylated peptide (Bt-AEGPPGPQG) [biotinylated on residue of 1 of SEQ ID NO: 14] was added to streptavidin (10 µg/mL) coated plates (Pierce Chemical) and 2 µL of each hybridoma supernatant added to 100 µL of DPBS (Gibco, Grand Island, N.Y.) with 0.05% TW-20 (Sigma). Elisa positive wells were detected by rabbit anti-mouse IgG-HRP (Jackson Immuno Research, West Grove, Pa.).

Positive wells in the Elisa were subjected to a second round of selection on the BIAcore. Wells were sought which produced antibodies having slow off rates on the BIAcore as determined using BIAevaluation version 2.1 software (Pharmacia Biosensor, Piscataway, N.J.). Streptavidin (Pierce Chemical) at 100 µg/mL was conjugated using the Pharmacia Amine Coupling Kit (Pharmacia Biosensor) to carboxylated dextran-coated biosensor chips (Pharmacia Biosensor) at pH 4.0 using a flow rate of 5 µL/minute for 35 minutes. Typically, 2000 RU was added. Peptide (100 ng/mL) biotinylated on residue of 1 of SEQ ID NO: 14 as set forth in the Sequence Listing, was passed over the streptavidin chip at a flow rate of 100 µl/minute for 10 seconds. Candidate supernatants containing antibody were passed over the chip (2 µL/minute for 30 seconds) and the amount of added antibody noted. The buffer was changed to HBS (Pharmacia Biosensor), and the dissociation rate noted for the next 80 seconds. The chip was cleaned with 0.1 N HCl for 30 seconds between each run to remove residual antibody and to clear any nonspecific binding. The off-rates were determined using BIAevaluation kinetic analysis software version 2.1. Clones with the slowest off rates were selected for further analysis. These clones included 9A4, 11F2 and 3H10.

Further characterization of these clones was performed as follows: Four preparations consisting of type I collagen, type I collagen cleaved by collagenase, type II collagen, and type II collagen cleaved by collagenase were each coupled to a separate flow cell on a BIA 2000 instrument. They were conjugated using the Pharmacia Amine Coupling Kit (Pharmacia Biosensor) to carboxylated dextran coated biosensor chips (Pharmacia Biosensor) at pH 4.0 using a flow rate of 5 μL/minute for 35 minutes. The four flow cells added 8000, 7000, 4000 and 4000 RU, respectively. The cells were washed with 0.1 N HCl to clean them of any uncoupled material and to clean them of any residual antibody between runs. All antibody preparations were purified by Protein G chromatography (Pharmacia Biotechnology, Piscataway, N.J.) and were run at 10 μg/mL. The total binding to each of the four surfaces was recorded. Antibody 9A4 was selected because it showed selective binding to collagenase-cleaved type II collagen (type I=11 RU; type II=280 RU) and lacked significant binding to uncleaved collagen (type I=3 RU; type II=6 RU).

After three rounds of subcloning by limiting dilution in HT media (Sigma) with 5% fetal calf serum (Hyclone), a stable 9A4 monoclonal hybridoma was obtained. It has been deposited with the American Type Culture Collection as ATCC-HB-12436.

EXAMPLE 2

Generation and Characterization of Monoclonal Antibody 5109.

Balb/c mice were immunized initially with the peptide having the sequence set forth in the Sequence Listing as SEQ ID NO: 18 (Anaspec, San Jose, Calif.) covalently linked to the KLH maleimide (Pierce Chemical) and administered in complete Freund's adjuvant (DIFCO). The mice were boosted monthly for about 5 months using incomplete Freund's adjuvant (DIFCO) until the titers were 1:100,000. Mice were boosted i.v. 10 days prior to fusion. Splenocytes were collected and fused with a non-Ig secreting cell-line derived from P3X63Ag8.653 cells (ATCC) using 50% PEG-1450 (ATCC). They were plated at $10^6$ cells/well in 96 well microtiter plates in HAT media (Sigma) with 15% fetal calf serum (Hyclone). Ten days later the wells were screened by Elisa. For identification of positive antibody producing wells, 10 ng/mL biotinylated peptide (biotinylated on residue 1 of SEQ ID NO: 19 as set forth in the Sequence Listing) was added to streptavidin (10 μg/mL) coated plates (Pierce Chemical) and 2 μL of each hybridoma supernatant added to 100 μL of DPBS with 0.05% TW-20 (Sigma). Elisa positive wells were detected by rabbit anti-mouse IgG-HRP (Jackson ImmunoResearch).

Positive wells were subjected to a second round of selection on the BIAcore for those which had antibodies giving the slowest off-rates on the BIAcore. Streptavidin (Pierce Chemical) at 100 μg/mL was conjugated using the Pharmacia Amine Coupling Kit (Pharmacia Biosensor) to carboxylated dextran coated biosensor chips (Pharmacia Biosensor) at pH 4.0 using a flow rate of 5 μl/minute for 35 minutes. Typically, 2000 RU was added. Peptide (100 ng/mL), biotinylated on residue 1 of SEQ ID NO: 19 as set forth in the Sequence Listing, was passed over the streptavidin chip at a flow rate of 100 μL/minute for 10 seconds. Supernatants containing antibody were passed over the chip (2 μL/minute for 30 seconds) and the amount of added antibody noted. The buffer was changed to HBS (Pharmacia Biosensor), and the dissociation rate noted for the next 80 seconds. The chip was cleaned with 0.1 N HCl for 30 seconds between each run to remove antibody and to get rid of any nonspecific binding. The off-rates were determined using the BIAevaluation software version 2.1. Clones with slow off-rates were sought. MAb 5109 was selected for further analysis.

Four preparations consisting of type I collagen, type I collagen cleaved by collagenase, type II collagen, and type II collagen cleaved by collagenase were each coupled to a single channel of a four channel BIAcore. These were conjugated using the Pharmacia Amine Coupling Kit (Pharmacia Biosensor) to carboxylated dextran coated biosensor chips (Pharmacia Biosensor) at pH 4.0 using a flow rate of 5 μL/minute for 35 minutes. The four flow cells added 8000, 7000, 4000 and 4000 RU, respectively. The cells were washed with 0.1 N HCl to clear them of any uncoupled material and to clear them of any specific materials between runs. All antibody preparations were purified by Protein G chromatography (Pharmacia Biotech), and run at 10 μg/mL. The total binding to each of the four surfaces was recorded. Antibody 5109 was selected because it showed selective binding to collagenase cleaved collagen (cleaved type I=23 RU; cleaved type II=173 RU), but lacked significant binding to uncleaved collagen (type I=23 RU; type II=15 RU). After nine rounds of subcloning by limiting dilution in HT media (Sigma) with 5% fetal calf serum (Hyclone), a stable 5109 monoclonal hybridoma was obtained. It has been deposited with the American type culture collection as ATCC-HB-12435.

EXAMPLE 3

Description of a Sandwich Assay Using 9A4 as the Capture Antibody and Monoclonal 5109 as the Detection Antibody.

Monoclonal antibody 9A4 (the capture antibody) was added to Nunc Maxisorp (VWR, Boston, Mass.) 96-well plates with 9A4 at 10 μg/mL in 0.05M sodium borate buffer, pH 8.5 using 100 μL/well (except for control wells numbered 4, 5 and 6, see Table 1) and incubated for 18–48 hours at 4° C.

The plate was washed three times with DPBS with 0.05% TW-20 (Sigma), (DPBS/TW-20); 200 μL/well was used.

Wells in the plate were blocked with 1% non-fat dry milk (NFDM) dissolved in DPBS (NFDM DPBS) prepared freshly, i.e., held on ice for no more than the day of use, using 100 μL/well incubated for 1 hour at RT.

The blocking solution was discarded, the wells rinsed one time with 200 μL of DPBS/TW-20.

Peptide 130 was diluted in 0.1% NFDM DPBS to concentrations shown in Table 1. Peptide 130 has the sequence set forth in the Sequence Listing as SEQ ID NO: 20 and was synthesized and purified by Anaspec Inc (San Jose, Calif.).

The dilutions of peptide 130 (SEQ ID NO: 20), the specimens at appropriate dilutions, and the controls were placed into the specified wells of the microtiter plate as shown in Table 1.

TABLE 1

Outline of the microtiter plate and antibody coating scheme

| | pep 130 (SEQ ID NO: 20) ng/mL | | | | | | | | | | | |
|---|---|---|---|---|---|---|---|---|---|---|---|---|
| pep 130 | 2 | 1.33 | 0.889 | 0.59 | 0.4 | 0.26 | 0.18 | 0.12 | 0.08 | 0.05 | 0.03 | 0.02 |
| | " | " | " | " | " | " | " | " | " | " | " | " |
| | smpl | smpl | smpl | smpl | smpl | smpl | smpl | smpl | smpl | smpl | smpl | smpl |
| | " | " | " | " | " | " | " | " | " | " | " | " |
| | " | " | " | " | " | " | " | " | " | " | " | " |
| | " | " | " | " | " | " | " | " | " | " | " | " |
| | " | " | " | " | " | " | " | " | " | " | " | " |
| cntrls. | 1 | 1 | 2 | 2 | 3 | 3 | 4 | 4 | 5 | 5 | 6 | 6 |

TABLE 2

Additions to the control wells

| Controls: | 9A4 | Biotinylated 130 | Anti-biotin antibody 5109 | HRP-labelled |
|---|---|---|---|---|
| 1 | + | − | − | + |
| 2 | + | + | − | + |
| 3 | + | − | + | + |
| 4 | − | + | + | + |
| 5 | − | + | − | + |
| 6 | − | − | + | + |

The wells were washed three times with 200 μL/well of DPBS TW-20.

Biotin-conjugated MAb 5109 (Bt-5109) was added to all peptide 130 (SEQ ID NO: 20) containing wells, all sample wells, and all control wells except 1,2, and 5. 5109-Bt (100 μL/well) at 1 μg/mL in 0.1% NFDM DPBS was added to each well and the plate incubated for 40 min at 37° C.

Note: MAb 5109 was biotinylated using 37 μg of biotin-N-hydroxysuccinamide (Pierce Chemical) per mg of MAb 5109 for 2 hrs and then dialyzed overnight using a 10 kD cut-off dialysis cassette (Pierce Chemical).

The wells were washed three times with 200 μL/well of DPBS TW-20.

Mouse monoclonal anti-biotin antibody conjugated with HRP (Jackson ImmunoResearch) was diluted 1/5000 in 0.1% NFDM DPBS and 100 μL/well was added to all wells and incubated for 30 minutes at RT.

The wells were washed three times with 200 μL/well with DPBS TW-20.

100 μL/well of 1-step Turbo (ready to use 3,3',5,5'-tetramethyl benzidine; Pierce Chemical) was added to each well and incubated at RT for approximately 10 minutes. Color development was stopped with 2N $H_2SO_4$. The results were read on a spectrophotometer at 450 nm.

TABLE 3

Standard curve data for 9A4 capture/Bt-5109 detection sandwich assay.

| | pep130 (SEQ ID NO: 20) | | | | lin regression | |
|---|---|---|---|---|---|---|
| | | log | | lin | | inter- |
| Cln7 | ng/mL | nM | nM | OD450 | regr slope | cept |
| 1 | 10 | 5.88 | 0.769 | 0.78 | 0.029 | 0.024 |
| 2 | 5 | 2.94 | 0.468 | 0.74 | | |
| 3 | 2.5 | 1.47 | 0.167 | 0.698 | | |
| 4 | 1.25 | 0.735 | −0.134 | 0.623 | 0.618 | |
| 5 | 0.625 | 0.368 | −0.435 | 0.483 | 0.474 | |
| 6 | 0.313 | 0.184 | −0.736 | 0.326 | 0.331 | |
| 7 | 0.156 | 0.092 | −1.037 | 0.151 | 0.187 | |
| 8 | 0.678 | 0.046 | −1.338 | 0.072 | 0.044 | |
| 9 | 0.039 | 0.023 | −1.639 | 0.039 | | |
| 10 | 0.020 | 0.011 | −1.94 | 0.005 | | |
| 11 | 0.010 | 0.006 | −2.24 | 1−5E-04 | | |
| 12 | 0 | 0 | | −0.006 | | |

From the concentrations of peptide 130 and the resulting optical density reading at 450 nm (Table 3), a standard curve was constructed (FIG. 1). Other appropriate peptides or collagen fragments can be substituted to prepare a standard curve analogous to FIG. 1. The units were expressed in terms of molar equivalents of standard. In this case, the units were nM equivalents of peptide 130 (SEQ ID NO: 20).

Over the linear portion of the curve, a regression line was used to fit the data. In the given case, the standard curve was linear between 0.735 nM and 0.46 nM when the concentrations are given in the log scale (as in the example, FIG. 1) and the regression curve is obtained using just the linear portion of the curve. For samples that fall outside of the linear portion, the concentrations can be read off the graph or the samples may be diluted to fall within the standard portion of the curve, or they may be below the limit of detection.

Figure 1. Standard curve of peptide 130 (SEQ ID NO: 20) and resulting optical density reading determined 9A4 Capture/Bt-5109 Sandwich Elisa.

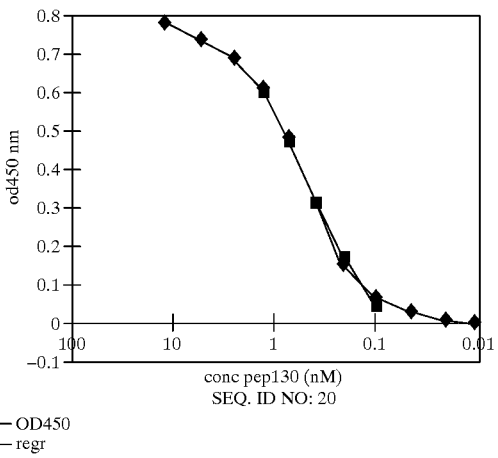

The regression between log (nM) and OD450 gives a slope of 0.029 OD450/log(nM) and an intercept of 0.024 OD450. When unknown samples are run, the calibration curve can be used to determine of concentration of collagenase-generated type II collagen fragments from the optical density of the sample. The following equation can be used:

Log(Concentration)=(Sample OD450−Intercept)/Slope

Sample:

In the given case, an unknown sample of synovial fluid had an OD450 of 0.229. Thus Log (Concentration)=(Sample OD450−0.024)/0.029=−0.949

Taking the anti-log, the concentration of fragment in synovial fluid=0.112 nM

EXAMPLE 4

Description of a Sandwich Assay Using Monoclonal Antibody 5109 as the Capture Antibody and 9A4 as the Detection Antibody.

Monoclonal antibody 5109 (the capture antibody) was added to Nunc Maxisorp (VWR, Boston, Mass.) 96-well plates with 5109 at 10 μg/mL in 0.05 M sodium borate buffer, pH 8.5, using 100 μL/well (except for control wells numbered 4, 5 and 6, see Table 4) and incubated for 18–48 hours at 4° C.

The plate was washed three times with 200 μL/well of DPBS TW-20.

Wells in the plate were blocked with 1% (NFDM) dissolved in DPBS prepared freshly using 100 μL/well incubated for 1 hour at room temperature.

The blocking solution was discarded, and the wells rinsed one time with 200 μL of DPBS/TW-20.

Peptide 130 (SEQ ID NO: 20) was diluted in 0.1% NFDM DPBS to concentrations shown in Table 4. Peptide 130 has the sequence set forth in the Sequence Listing as SEQ ID NO: 20 and was synthesized and purified by Anaspec Inc (San Jose, Calif.).

The dilutions of peptide 130 (SEQ ID NO: 20), the unknown specimens at appropriate dilutions, and the controls were placed into the specified wells of the microtiter plate as shown in Table 4.

TABLE 4

Outline of the microtiter plate and antibody coating scheme

| pep 130 (SEQ ID NO: 20) ng/mL | | | | | | | | | | | | |
|---|---|---|---|---|---|---|---|---|---|---|---|---|
| pep 130 | 2 | 1.33 | 0.889 | 0.59 | 0.4 | 0.26 | 0.18 | 0.12 | 0.08 | 0.05 | 0.03 | 0.02 |
| | " | " | " | " | " | " | " | " | " | " | " | " |
| | smpl | smpl | smpl | smpl | smpl | smpl | smpl | smpl | smpl | smpl | smpl | smpl |
| | " | " | " | " | " | " | " | " | " | " | " | " |
| | " | " | " | " | " | " | " | " | " | " | " | " |
| | " | " | " | " | " | " | " | " | " | " | " | " |
| | " | " | " | " | " | " | " | " | " | " | " | " |
| cntrls. | 1 | 1 | 2 | 2 | 3 | 3 | 4 | 4 | 5 | 5 | 6 | 6 |

TABLE 5

Additions to the control wells

| Controls: | | Biotinylated | Anti-biotin antibody |
|---|---|---|---|
| | 5109 | 130 | 9A4 | HRP-labelled |
| 1 | + | − | − | + |
| 2 | + | + | − | + |
| 3 | + | − | + | + |
| 4 | − | + | + | + |
| 5 | − | + | − | + |
| 6 | − | − | + | + |

The wells were washed three times with 200 μL/well of DPBS TW-20.

Biotin conjugated monoclonal antibody 9A4 (Bt-9A4) was added to all peptide 130 (SEQ ID NO: 20) containing wells, all sample wells, and all control wells except 1,2, and 5. 100 μL/well of 9A4-Bt at 1 μg/mL in 0.1% NFDM DPBS was added to each well and the plate incubated for 40 min at 37° C.

Note: 9A4 was biotinylated using 37 μg of biotin-N-hydroxysuccinamide (Pierce Chemical) per mg of monoclonal antibody 9A4 for 2 hrs and then dialyzed over night using a 10 kD cut-off dialysis cassette (Pierce Chemical).

The wells were washed three times with 200 μL/well of DPBS TW-20.

Mouse monoclonal anti-biotin antibody conjugated with HRP (Jackson ImmunoResearch) was diluted 1/5000 in 0.1% NFDM DPBS and 100 μL/well was added to all wells and incubated for 30 minutes at RT.

The wells were washed three times with 200 μL/well of DPBS TW-20.

One hundred microliters/well of 1-step Turbo (ready to use 3,3',5,5'-tetramethyl benzidine; Pierce Chemical) was added to each well and incubated at RT for approximately 10 minutes. Color development was stopped with 2N $H_2SO_4$. The results were read with a spectrophotometer at 450 nm.

TABLE 6

Standard curve data for 5109 capture/Bt-9A4 detection sandwich assay

| | pep130 (SEQ ID NO: 20) | log | | | lin regr | lin regression | |
|---|---|---|---|---|---|---|---|
| Cln7 | ng/mL | nM | nM | OD450 | | slope | intercept |
| 1 | 10 | 5.88 | 0.769 | 9.64 | | 0.42 | 0.70 |
| 2 | 5 | 2.94 | 0.468 | 0.65 | | | |
| 3 | 2.5 | 1.47 | 0.167 | 0.62 | | | |
| 4 | 1.25 | 0.735 | −0.134 | 0.61 | | | |
| 5 | 0.625 | 0.368 | −0.435 | 0.57 | | | |
| 6 | 0.313 | 0.184 | −0.736 | 0.52 | 0.52 | | |
| 7 | 0.156 | 0.092 | −1.037 | 0.40 | 0.39 | | |
| 8 | 0.078 | 0.046 | −1.338 | 0.23 | 0.26 | | |
| 9 | 0.039 | 0.023 | −1.639 | 0.11 | 0.13 | | |
| 10 | 0.020 | 0.011 | −1.94 | 0.04 | 0 | | |
| 11 | 0.010 | 0.006 | −2.241 | 0.01 | | | |
| 12 | 0 | 0 | | −0.01 | | | |

From the concentrations of peptide 130 (SEQ ID NO: 20) and the resulting optical density reading at 450 nm, a standard curve was constructed. Again, other appopriate peptides or collagen fragments could be utilized to prepare a standard curve. The units needed were expressed in terms of equivalents of standard. In this case, the units were appropriate in terms of nM equivalents of peptide 130 (SEQ ID 20).

Over the linear portion of the curve, a regression line was used to fit the data. In the given case, the standard curve was linear between 0.3125 nM and 0.0195 nM when the concentrations were given in the log scale (as in the example Figure) and the regression curve was obtained using just the linear portion of the curve. For samples that fall outside of the linear portion, the concentrations can be read off the graph or the samples may be diluted to fall within the standard portion of the curve, or the concentration of collagen fragments in the samples may be below the detection limit.

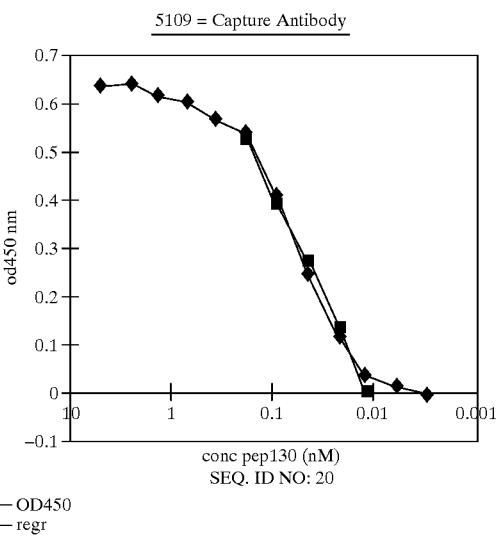

Figure 2. Standard curve for 5109 capture/Bt-9A4 detection sandwich assay.

The regression between log (nM) and OD450 nm gives a slope of 0.42 OD450/log(nM) and an intercept of 0.70 OD450 nm. When samples are run, the calibration curve can be used to determine the concentration of collagen fragment from the optical density of the sample.

Samples:

In the given case, the unknown sample of human urine from an arthritic patient has an OD450 of 0.124

Log(Concentration)=(Sample OD450−0.70)/0.42=−1.36

Taking the anti-log, the concentration of fragment in urine= 0.44 nM

In another case, the standard curve gave a slope of 0.249 and an intercept of 0.638. An unknown sample of human osteoarthritis plasma had an OD450 nm of 0.172. The sample of osteoarthritic plasma had a concentration of 68 pM.

EXAMPLE 5

Antibody 5109 can be used Directly to Measure the Amounts of Type II Collagen Fragment in a Competition Assay.

In an adaptation of concentration analysis (*BIAapplications Handbook*, Pharmacia Biosensor, June, 1994 Edition, p. 6-2 to 6-9), streptavidin (Pierce Chemical, Rockford, Ill.) at 100 μg/mL was conjugated with the Pharmacia Amine Coupling Kit (Pharmacia Biosensor) to carboxylated dextran coated biosensor chips (Pharmacia Biosensor) at pH 4.0 using a flow rate of 5 μL/minute for 35 minutes. Typically, 2000 RU was added. Biotinylated peptide (100 ng/mL) having the sequence set forth in the Sequence Listing as SEQ ID NO: 19 was passed over the streptavidin chip at a flow rate of 5 μL/minute for 2 minutes; 144 RU of peptide was added to the streptavidin surface. MAb 5109 at a concentration of 6.3 μg/mL either alone or in mixtures with standard concentrations of peptide 054 (SEQ ID NO: 19) or mixtures of 5109 and dilutions of samples with unknown amounts of collagen fragments were passed over the peptide surface for 1 minute at a flow rate of 10 μL/min. The slopes of the linear portions of the association phase for each curve were analyzed with BIAevaluation version 2.1 software. A standard curve of competing peptide 054 (SEQ ID NO: 19) vs slope was constructed. The amount of collagen epitope in the samples was determined by comparison of a sample's slope to the slopes of the standard curve to calculate the amount of epitope. Between each injection, the chip was cleaned with 0.1 N HCl for 30 seconds to remove antibody.

TABLE 7

5109 mixed with standard amounts of peptide 054 (SEQ ID NO: 19).

| | Dil. of pep054 M | log M | rO slope | linear regression values |
|---|---|---|---|---|
| 1 | 1.34E-06 | −5.87 | 0.187 | |
| 2 | 6.71E-07 | −6.17 | 0.208 | |
| 3 | 3.36E-07 | −6.47 | 0.375 | |
| 4 | 1.68E-07 | −6.78 | 0.729 | 2.16 |
| 5 | 8.39E-08 | −7.08 | 12.7 | 10.09 |
| 6 | 4.19E-08 | −7.38 | 17.1 | 18.03 |
| 7 | 2.10E-08 | −7.68 | 25.7 | 25.96 |
| 8 | 1.05E-08 | −7.98 | 22.5 | |
| 9 | 5.24E-09 | −8.28 | 26.6 | |
| 10 | 2.62E-09 | −8.58 | 24.0 | |

TABLE 7-continued 5109 mixed with standard amounts of peptide 054 (SEQ ID NO: 19).

| | Dil. of pep054 M | log M | rO slope | linear regression values |
|---|---|---|---|---|
| 11 | 1.31E-09 | −8.88 | 26.6 | |
| 12 | 6.55E-10 | −9.18 | 25.6 | |
| 13 | 0 | | 23 | |

Linear regression slope = −26.36
y-intercept = −176

Figure 3.

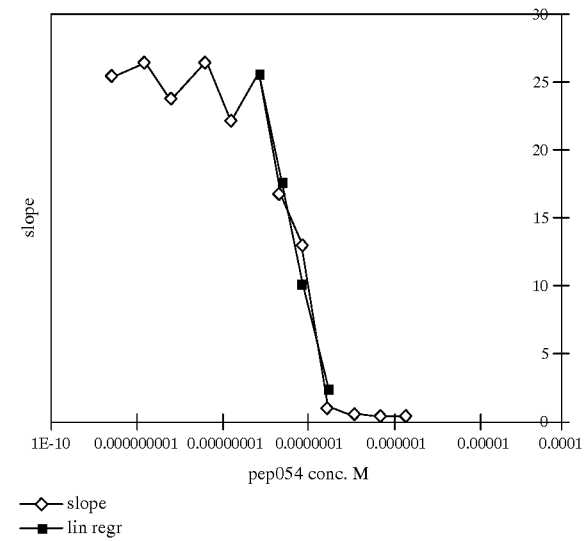

Standard curve:
Inhibition of 5109a binding by pep054 (SEQ ID No: 19)
slope vs 054 conc —◇— slope
—■— lin regr Sample:

Supernatant of a collagenase-3 MMP13 digest of bovine nasal cartilage. The sample was run over the BIAcore chip diluted 2-fold, 4-fold and 8-fold. The calculated amounts of collagen in terms of 054 peptide (SEQ ID NO: 19) were determined. The results are given in column 4 of Table 8. After multiplying by the titer, a molar concentration (M) of collagen can be determined in terms of the peptide 054 (SEQ ID NO: 19) standard.

TABLE 8

The titer and concentrations of the unknown sample in terms of peptide 054 (SEQ ID NO: 19) concentration.

| | titer | slope | M (054) | nM (054) |
|---|---|---|---|---|
| 5109 | alone | 6.648 | Background | |
| 5109 + | 1:2 | 3.539 | 4E-08 | 80 |
| 5109 + | 1:4 | 4.885 | 2E-08 | 80 |
| 5109 + | 1:8 | 5.825 | 8E-09 | 64 |

The consistency of the results (last column) after correction for dilution is shown by the agreement of the values calculated from the three separate dilutions (next to last column) of the unknown samples. An average value of 75 nM type II collagen fragments is obtained for the bovine nasal cartilage supernatant.

EXAMPLE 6

Preparation of Genetically Engineered Antibodies Related to 9A4.

The basis for generating engineered antibodies and their subsequent evaluation as biologically active or relevant molecules is the cloning, assembly configuration and characterization of the $V_L$ and $V_H$ domains of the parent antibody. We have determined the $V_L$ and $V_H$ structural sequences of the subject antibodies and the uniqueness of the particular $V_L$-$V_H$ combination that forms the active binding site to the antigens described in this invention. Before cloning the 9A4 variable region genes, it was necessary to determine the protein sequence of portions of the variable domains of the parent 9A4 IgG1 antibody so that when the variable domains were cloned, it could be ascertained that the correct variable domains were indeed obtained and not other ones derived from the myeloma fusion partner or an inactive pseudogene from the B-cell used in generating the hybridoma. Culture supernatant containing 9A4 IgG1 was generated by growing the 9A4 hybridoma in roller bottles. Supernatants were adjusted to pH 7.5 with dibasic sodium phosphate and the salt concentration adjusted with 3 M sodium chloride to a final concentration of 150 mM. Filtered (0.2 μ) supernatant was passed through a 15 mL bed volume of Protein G (Pharmacia) at a flow rate of 20 mL/min. After further washing the column with 150 mM NaCl solution, the antibody was eluted with 100 mM glycine pH 3.1. The antibody was isotyped using anti-sera from the Mouse Immunoglobulin Isotyping Kit (Boehringer Mannheim, Indianapolis, Ind.) and found to be an IgG1 class murine antibody with a kappa light chain.

It has been observed that some isolated proteins are "blocked" at their amino terminus. By "blocked" is meant that the amino acid residue at the amino terminus of the polypeptide chain has been chemically modified in its structure posttranslationally by cellular action or some spontaneous chemical change in such a way that the polypeptide chain is resistant to Edman degradation. The Edman degradation method is the chemical procedure routinely used over the past 40 years for determining the amino acid sequence of proteins. Use of the Edman degradation technique, normally automated in a laboratory instrument known as a sequenator or protein sequencer, is a standard procedure well known to those skilled in the art of protein biochemistry.

A common mode of blocking is conversion of an amino-terminal glutaminyl residue into a pyroglutamyl residue. This occurs by cyclization of the glutaminyl residue to form a structure which is inaccessible to the Edman reaction because a new amide linkage is formed between the former alpha-amino group and the delta-carboxyl group. In such circumstances, the ability to obtain sequence information from the amino terminus of the protein depends on removal of the pyroglutamyl residue by a chemical or enzymatic method. An important method is to use an enzyme called pyroglutamate aminopeptidase (EC 3.4.19.3) to remove the pyroglutamyl residue. The blocked protein, which may be in solution or electroblotted to a membrane material such as PVDF (polyvinylidene difluoride), is treated with a solution of pyroglutamate aminopeptidase until a sufficient amount of the protein has been unblocked to allow successful determination of the amino acid sequence by automated Edman chemistry. Example methods for this are described in: Fowler E F, Moyer M, Krishna R G, Chin C C Q and Wold F, (1995) "Removal of N-Terminal Blocking Groups from Proteins" in Current Protocols in Protein Science., pp.11.7.1–11.7.17 (eds. Coligan J E, Dunn B M, Ploegh H L, Speicher D W., & Wingfield P T.), John Wiley, New York.

In the present work, the heavy and light chains of MAb 9A4 were separated by SDS-polyacrylamide gel electrophoresis with the use of a reducing agent (beta-mercaptoethanol) in the sample buffer. Following electrophoresis, polypeptides in the gel were electroblotted to a PVDF membrane and detected by staining with Coomassie Brilliant Blue R-250. Bands containing the heavy and light chains of 9A4 were then excised from the blot and separately treated with pyroglutamate aminopeptidase. In each case, it proved possible subsequent to this treatment to obtain amino-terminal sequence information by Edman degradation. Sequencing was performed on a Perkin-Elmer Applied Biosystems Model 494 Procise protein sequencer.

When it is desired to obtain internal (i.e. not N-terminal) amino acid sequence information from the protein, blotted samples of the protein may be digested with trypsin and the resulting digest fractionated by HPLC to afford individual peptides which may then be sequenced.

Specifics of the work were as follows:

N-terminal De-blocking with Pyroglutamate Aminopeptidase (PGAP)

Antibody (9A4) was separated into its constituent heavy and light chains by SDS-PAGE on a Tris-Gly 4–20% polyacrylamide gel (Novex, San Diego). It was then electroblotted onto ProBlott (Perkin-Elmer Applied Biosystems, Foster City, Calif.) and the bands were visualized by Ponceau S (Sigma) staining.

The membranes containing 9A4 light chain were excised and incubated for 30 min in a buffer containing: 0.1 M sodium phosphate, 10 mM $Na_2EDTA$, 5 mM dithioerythritol, 5% glycerol, and 0.1% reduced Triton X-100. Pyroglutamate aminopeptidase (20 mg)(Boehringer Mannheim, Indianapolis, Ind.) was added to the vial, the contents mixed gently, and the reaction was incubated overnight at 37° C. The membranes were removed and washed extensively in water to remove all salts, detergent and enzyme. The membranes were then placed in the Applied Biosystems Model 494 protein sequencer (Perkin-Elmer) for N-terminal sequence analysis according to the directions provided by the manufacturer.

The heavy chain was treated in the same manner as above for the light chain.

Then follwing N-terminal sequence results were obtained:

| Sample | Sequence data file | Sequence |
| --- | --- | --- |
| Light chain | 9A4L_7 3-22-96 | IVLTQSPVFMSASPGEKVTM (Note 1) |
| Heavy chain | 9A4H_4 3-26-96 | IQLVQSGPELKKPGQTVKI(S) (Note 2) |

Residues in parenthesis indicate tentative calls.
Note 1: This sequence corresponds to residues 9 to 28 of SEQ ID NO: 33.
Note 2: This sequence corresponds to residues 13 to 32 of SEQ ID NO: 32.

In addition to the N-terminal sequence data obtained above, internal sequencing of the 9A4 antibody light chain was also performed, according to the method developed from:

Fernandez J, Andrews L, Mische S M, Anal Biochem 1994; 218: 112–117.

Four bands corresponding to the 9A4 light chain were excised from the ProBlott and incubated for 30 min in a buffer containing 10% acetonitrile, and 0.1% reduced Triton X-100 in 0.1 M Tris-HCl pH 8.8. Sequencing Grade Modified Trypsin (0.2 mg)(Promega, Madison, Wis.) was added and the bands were incubated overnight at 37° C. The resulting peptides were extracted from the membrane by washing with 60% acetonitrile, 0.1% TFA, $H_2O$ and sonication. The peptides were separated by RP-HPLC on a Vydac C18 218TP column (1.0×250 cm)(Vydac, Hesperia, Calif.). The peaks were collected visually by hand and selected peaks were analyzed by automated Edman sequencing on a Model 494 protein sequencer as above.
The following N-terminal sequence results for the peptide fragments were obtained:

| Sequence data file | Sequence |
| --- | --- |
| 9A4L_10 | DSTYSMSSTL ($C_K$ sequence) |
| 9A4L_12 | LLIHATSNLASGVPVR (Note 1) |
| 9A4L_13 | FSGGGSGTSYSLTISR (Note 2) |
| 9A4L_14 | XFNR ($C_K$ sequence) |
| 9A4L_15 | (H)NSYTCEATHK ($C_K$ sequence) |
| 9A4L_16 | (Q)NGVLNGTSY ($C_K$ sequence) |
| 9A4L_17 | LEIIR (Note 3) |

Residues in parenthesis indicate tentative calls.
Note 1: This sequence corresponds to residues 52 to 67 of SEQ ID NO: 33.
Note 2: This sequence corresponds to residues 68 to 83 of SEQ ID NO: 33.
Note 3: This sequence corresponds to residues 110 to 114 of SEQ ID NO: 33.

Mature 9A4 Light Chain ($V_L$–$C_{kappa}$) Amino Acid Sequence (comparison of sequence derived from DNA sequencing of the cloned $V_L$ (see below) and the murine $C_{kappa}$ (obtained from Kabat E A, Wutt, Perry H M, Bottesman K S and Foeller C.—"Sequences of Proteins of Immunological Interest, U.S. Department of Health and Human Services, NIH, 5th Edition, publication #91-3242, 1991) with sequences obtained by Edman degradation)

to those skilled in the art that this would not prevent annealing and subsequent generation of cDNA.

Note: Oligos were synthesized by Oligos Etc (Wilsonville, Oreg.), Genosys (The Woodlands, Tex.) or Perkin-Elmer Applied Biosystems (Foster City, Calif.).

The amino terminal amino acid sequence data was used to generate a possible oligo to isolate the correct 9A4 $V_H$ gene by PCR as follows. Based on the 20 amino acid sequence presented above for the $V_H$ amino terminal region, which corresponds to residues 13 to 32 of SEQ ID NO: 32, and assuming that the amino terminal amino acid of the mature form of the secreted antibody heavy chain was indeed a Gln residue [residue 12 of SEQ. ID. NO. 32], sequences of known antibodies were compared to that of 9A4 $V_H$ using the Kabat data base: Sequences of Proteins of Immunological Interest, Volume II, 1991. Antibody $V_H$ domains that matched the first 20 amino acids of the mature 9A4 $V_H$ included: MAb 264 (Nottenburg C, St. John T, and Weissman I L J Immunol 1987;139: 1718–1726); MAbRFT2 (Heinrich G, Gram H, Hocher H P, Schreier M H, Ryffel B, Akbar A, Amlot P L, and Janossy G, J Immunol 1989; 143: 3589–3597; and MAb2H1 (Li Y-W, Lawrie D K, Thammana P, Moore G P and Shearman C W, Mol Immunol 1990; 27: 303–311). Since it is important to obtain the original DNA sequence corresponding to the amino terminus of the mature antibody, the 5' PCR oligo should be designed to anneal 5' (upstream) from the amino terminus, i.e. in the signal peptide segment. The DNA sequences of all the above 3 antibodies, with which the first 20 amino acids of the 9A4 $V_H$ was identical, had known signal peptide DNA and amino acid sequences. The DNA sequences are shown here: (Underlined nucleotides indicate differences between the sequences).

```
  1 QIVLTQSPVF MSASPGEKVT MTCSASSSVS YMYWYQQKPG SSPRLLIHAT SNLASGVPVR
 61 FSGGGSGTSY SLTISRMEAE DAATYYCQQW RSYTRTFGGG TKLEII*RADA APTVSIFPPS
121 SEQLTSGGAS VVCFLNNFYP KDINVKWKID GSERQNGVLN SWTDQDSKDS TYSMSSTLTL
181 TKDEYERHNS YTCEATHKTS TSPIVKSFNR NEC
```
Underlined amino acids have been sequenced by automated Edman sequencing [Also see table above]. The sequence obtained from the cloned DNA, when compared with the amino acid sequences from the fragments of the original antibody protein shown above, indicates that the gene cloned is the correct one for the 9A4 $V_L$.
*Amino acid 106 above is usually a Lys residue in the J1 germline segment, but has been mutated to the Ile residue shown above for the 9A4 $V_L$. Amino acid 106 marks the end of the $V_L$ domain while amino acid 107 (Arg) marks the beginning of the C kappa domain.

Cloning and Determination of the $V_L$ and $V_H$ Sequences of MAb 9A4

The 9A4 hybridoma cell line was grown in HT media (Sigma) with 5% fetal calf serum (Hyclone). mRNA was extracted from a cell pellet containing 1×10⁷ cells using the Pharmacia Quick Prep mRNA Extraction Kit (Pharmacia) as per the manufacturer's protocol. cDNA was then synthesized for both the $V_L$ and $V_H$ gene segments using Boehringer Mannheim's cDNA Kit (Indianapolis, Ind.) as per the protocol provided by the manufacturer. The oligo used in the $V_L$ cDNA reaction (named MLK) and set forth in the Sequence Listing as SEQ ID NO: 21 was specific for the murine light chain kappa region, while the oligo used in the $V_H$ cDNA reaction was specific for a segment in the $C_H2$ domain of the murine heavy chain gamma region was named MHG. The sequence of MHG is set forth in the Sequence Listing as SEQ ID NO: 22. This oligo was designed to anneal to all 4 murine IgG isotypes, including IgG1, IgG2a, IgG2b and IgG3. There is a single base mismatch for IgG1 at nucleotide 5 of SEQ ID NO: 22, but it should be apparent

```
                                      (SEQ ID NO: 23)
  264:  5'- GG CTG TGG AAC TTG CTA TTC (SEQ ID NO: 24)
 RFT2:  5'- GG GTG TGG ACC TTG CCA TTC (SEQ ID NO: 25)
  2H1:  5'- GG GTG TGG ACC TTG CTA TTC
```

These sequences code for amino acids −11 to −17 in the signal peptides for the $V_H$s of the corresponding antibodies [Kabat]. The 5' oligo, MHMISC was thus designed to isolate the genuine 9A4 $V_H$. The sequence of MHMISC is set forth in the Sequence Listing as SEQ ID NO: 26.

For isolating the 9A4 $V_L$, a series of five degenerate oligo sets were designed to anneal to the leader peptide segments of known murine kappa light chains. These oligos were employed in 5 separate PCR amplifications. (See below). The sequences of the 5 degenerate oligo sets were provided by The Dow Chemical Company (Midland Mich.) and are hereby acknowledged. The 5' oligo set that gave a bona fide 9A4 $V_L$ was MK3, the sequence of which is set forth in the Sequence Listing as SEQ ID NO: 27. These oligos code for residues −8 to −14 in the signal peptide.

The reverse primers for the $V_L$ and $V_H$ PCRs were designed from known sequences of the murine IgG1 heavy chain constant region (from the $C_H1$ domain), called MIGG1CH1, the sequence of which is set forth in the Sequence Listing as SEQ ID NO: 28, and the constant region of the kappa light chain, called MLKN, the sequence of which is set forth in the Sequence Listing as SEQ ID NO: 29. These oligos were nested (upstream) relative to the 3' primers used in the cDNA synthesis.

The annealing segment begins at nucleotide 10 of SEQ ID NO: 29.

The 9A4 $V_H$ and $V_L$ genes were amplified by PCR using the corresponding oligos described above and 0.41 μg of 9A4 hybridoma cDNA. The PCR was set up using a GeneAmp® Kit with Native Taq Polymerase (Perkin Elmer) and used according to the manufacturer's specifications. The temperatures of denaturation, annealing and polymerization were 94° C., 55° C., and 72° C. for 45 s, 45 s, and 60 s seconds, respectively for the $V_H$ PCR and for the $V_L$ PCR the annealing temperature was changed to 60° C. The PCR was carried out for 36 cycles plus a final polymerization cyde of 72° C. for 7 min followed by a 4° C. hold. The PCR products were cloned in the pCR2.1 vector (Invitrogen, Carlsbad, Calif.) and also sequenced to determine and verify the DNA and derived amino acid sequences of the $V_L$ and $V_H$. The oligos used for sequence determination were MK3 and MLKN for the $V_L$ and MIGG1CH1 for the $V_H$ and are set forth in the Sequence Listing as SEQ ID NOS: 27, 29 and 28, respectively.

The DNA sequences corresponding to 9A4 $V_H$ and $V_L$ are set forth in the Sequence Listing as SEQ ID NOS: 5 and 6, respectively. The derived amino acid sequences of the 9A4 $V_H$ and $V_L$ genes are set forth separately in the Sequence Listing as SEQ ID NOS: 32 and 33, respectively.

Surprisingly, the oligo MHMISC (SEQ ID NO: 26) successfully provided a $V_H$ sequence which corresponded exactly to the first 20 amino acids of the mature protein $V_H$ determined by protein sequencing of 9A4 IgG1. Immediately 3' of the 5' PCR oligo, MHMISC (SEQ ID NO: 26), the DNA sequence in the leader peptide segment of the 9A4 $V_H$ is almost identical to the corresponding segment of MAb 2H1, and is likely therefore to be derived from the same germline $V_H$ gene as 2H1. There are only 3 differences in amino acid sequence between the 2 antibodies in the $V_H$ regions; 1 in CDR1, 1 in CDR2 and 1 in FR3. These are likely somatic mutations that have occurred during the affinity maturation process for these two antibodies and may play a role in defining the specificity and affinity of each of the antibodies for their respective targets. The 9A4 $V_H$ utilizes the murine $J_H2$ joining segment gene and codes for residues 114 (within the CDR3) to 126 of SEQ ID NO: 32.

The 9A4 variable heavy chain belongs to Kabat's Mouse Ig heavy chain Family II. (The $V_H$ genes here identified were taken from the Kabat Database at http://immuno.bme.nwu.edu/famgroup.html). The 9A4 $V_H$ heavy chain (SEQ ID NO: 5) most closely resembles Database ID number 001246. There are only 2 differences in these 2 $V_H$ genes, one occuring in the FR1 (silent mutation) and the other in the CDR1, at amino acid position 45 (SEQ ID NO: 32) where 9A4 has an Ile and 001246 has a Met. It is most likely that both of these genes are also derived from the same germline $V_H$.

We claim $V_H$ genes in other antibodies related to the 9A4 $V_H$ germline gene, such that when the $V_H$ gene product forms a productive antibody $V_L$-$V_H$ pair with the $V_L$ of this other antibody, it binds in a manner (specificity and affinity) analogous to 9A4.

The 9A4 $V_L$ gene and derived amino acid sequences are set forth in the Sequence Listing as SEQ ID NOS: 6 and 33, respectively. The derived amino acid sequence of the 9A4 $V_L$ gene matches all the peptide fragments from protein sequencing of genuine 9A4 light chain as presented above. The 9A4 variable light chain belongs to Kabat's Mouse Kappa Family XI and is most similar to Database ID Number 006306. There are 10 nudeotide mismatches, resulting in 7 amino acid differences. Two of these differences occur in FR1, 2 in CDR2, 1 in FR3 and 2 in CDR3. Since the majority of the changes occur in the CDRs, it is most likely that these 2 genes are related by being derived from the same or at least very similar germine $V_L$.

We claim $V_L$ genes in other antibodies derived or related to the 9A4 $V_L$ germline gene, such that when the $V_L$ gene product forms a productive antibody $V_L$-$V_H$ pair with the $V_H$ of this other antibody, it binds in a manner (specificity and affinity) analogous to 9A4.

We also claim antibodies where both the $V_L$ and $V_H$ are derived from the 9A4 $V_L$ and $V_H$ germline genes, disclosed herein, such that when the $V_L$ and $V_H$ gene products form a productive $V_L$-$V_H$ pair, this other or different antibody from 9A4 essentially binds in a manner (specificity and affinity) analogous to 9A4.

We now have the basis from which to design and construct genetically engineered versions of the subject invention 9A4 antibody. Two examples are presented below, both single chain antibodies (scFv). In one case, the design is $V_H$-Linker-$V_L$-HIS-MYC tags in the vector pCANTAB6 and in the other the scFv is constructed in the opposite orientation with a different linker, that is, $V_L$-Linker-$V_H$-FLAG tag, in the vector pATDFLAG. These examples are not meant to be limiting, but to those skilled in the art, it will readily be apparent that the newly characterized $V_H$ and $V_L$ domains of 9A4 (SEQ ID NOS: 5 and 6) can be utilized in part or in whole to obtain previously described antibody types, such as Fab's, or novel configurations that utilize only some critical portion of the V domains.

Construction of 9A4 scFv ($V_H$-linker-$V_L$) in pCANTAB6

SOEing (Splicing by Overlap Extension) PCR primers were utilized to prepare for assembly of the $V_H$ and $V_L$ fragments into a scFv antibody.

Two primers were designed and obtained from Perkin Elmer for the $V_H$ region: for the 5'$V_H$ end primer an Sfi I site was added while at the 3' end for the $V_H$ primer, an overlapping sequence with the $(Gly_4Ser)_3$ linker was added. The 5'$V_H$ primer was called 9A4VH5CAN and the 3'$V_H$ primer was called 9A4H3CAN, which correspond to SEQ ID NOS: 34 and 35 in the Sequence Listing.

For the $V_L$, a 5' end primer with overlap into the $Gly_4Ser$ linker region and a 3' primer incorporating a Not I restriction site were designed and also obtained from Perkin Elmer. The 5' primer was called 9A4VL5CAN and the 3'$V_L$ primer was called 9A4VL3CANILE, which correspond to SEQ ID NOS: 36 and 37 in the Sequence Listing.

The $V_H$ and $V_L$ DNA components were amplified by PCR and joined subsequently by an assembly, pull-through SOE-PCR step. Following the SOE-PCR reaction, a band in an agarose gel, which was identified to be ~700 bp, was excised and gel purified using the QIAquick Gel Purification Kit (QIAgen) as per the manufacturer's directions. The resulting DNA was digested with Sfi I and Not I and used in a ligation with the pCANTAB6 vector DNA (obtained from Cambridge Antibody Technology, Melbourne, Cambridgeshire, UK) which was also digested with the same restriction enzymes. The ligated DNA was then used to transform competent *E. coli* TG1 cells by electroporation. The basic protocol for generating the competent *E. coli* TG1 cells was as follows:

2YT media (Bio101, LaJolla, Calif.)500 mL prewarmed to 37° C. in a 2 L conical flask was inoculated with 2.5 mL of fresh overnight culture of TG1 cells. They were grown with vigorous aeration (300 rpm) at 37° C. until the OD at 600 nm was 0.2 to 0.25, usually 1–1.5 h. later. The flasks were chilled for 30 min on ice, then poured into 250 mL centrifuge bottles and spun at 4,000 rpm for 15 min in a prechilled (4° C.) Sorvall centrifuge to pellet the cells. The cells were resuspended in the original volume of prechilled water, and spun again as above to pellet the cells.

The cells were resuspended in half the original volume, i.e. 250 mL of prechilled water and left on ice for 3 min, were resuspended and spun again as above.

The cells were then resuspended in 20 mL of prechilled 10% glycerol, transferred to a prechilled 50 mL Falcon tube, left on ice for 15 min, and centrifuged at 3,500 rpm, at 4° C. for 10 min in a benchtop centrifuge.

The cells were finally resuspended in 1.0–2.5 mL prechilled 10% glycerol and used directly in the electroporation step.

Ligated DNA (25–250 ng pCANTAB6-Sfi I/Not I vector with 9A4$V_H$-L-$V_L$-Sfi I/Not I) was electroporated into the competent *E. coli* TG1 cells as follows:

The ligated DNA was ethanol precipitated per standard protocol. The DNA pellet was dissolved in 10 $\mu$L of sterile deionized distilled water.

The DNA (up to 10% of the total cell volume) was added to 100 $\mu$L of cells and transferred to a prechilled electroporation cuvette (Biorad) and left on ice.

The electroporation Gene Pulser apparatus (Biorad) parameters were set to 25 $\mu$FD, 2.5 kV and the pulse controller set to 200 ohms. The cuvette was dried with a tissue, placed in the electroporation chamber and pulsed once. Time constants in the 3.5–4.8 msec range were typically obtained. The electroporated cells were immediately diluted with 1 mL of 2YT medium supplemented with 2% glucose. The cells were transferred to a 15 mL Falcon tube and shook at 37° C. for 1 h.

The transformed cell mixture (20–1000 $\mu$L) was plated on appropriate size agar media plates containing 2YT, 2% Glucose and 100 ug/mL ampicillin (2YTAG).

Initially, a clone was obtained (p9A4ICAT3-2) that had a 5 base insertion at the Not I site, which put the downstream sequence out-of-frame. In order to correct this, a new oligo was made called 9A4NOTFIX3, the sequence of which is set forth in the Sequence Listing as SEQ ID NO: 38.

A PCR amplification using *E. coli* cells containing p9A4ICAT3-2 as the target for the annealing oligos was performed using the Advantage KlenTaq Polymerase Mix (Clontech, Palo Alto, Calif.) as per the manufacturer's protocol. The annealing oligos (35 pmol each) were 9A4NOTFIX3 and pUC19R. The sequence of pUC19R is set forth in the Sequence Listing as SEQ ID No. 39; it anneals upstream from the Sfi I site.

The PCR cycles (in a Perkin Elmer Cetus Model 9600 thermal cycler) were set up as follows: For the first cycle, denaturation of DNA was for 1 min at 94° C., annealing for 45 s at 60° C. and polymerization for 1.5 min at 68° C. For cycles 2–31, the same temperatures and times were used, except the denaturation times were reduced to 30 s. For the final cycle (32) the polymerization was set up for 5 min, after which time the cycler cooled the sample to 4° C. The TA cloning system (Invitrogen) was used to clone the resulting PCR products in the plasmid pCR2.1 using the protocol suggested by the manufacturer. Twelve white colonies were screened for inserts using the oligos M13 Forward and M13 Reverse (Invitrogen) (as set forth in the Sequence Listing as SEQ. ID. NOS. 53 and 54, respectively) by PCR using KlenTaq Polymerase as above. Three colonies produced inserts of the correct size on agarose gel electrophoresis. One of these with the correct DNA sequence for the 9A4 $V_H$-Linker-$V_L$ construct was chosen for further work. The DNA insert containing the scFv gene was obtained by digestion of the pCR2.1 derivative with Sfi I and Not I, purified using the QIAquick Gel Extraction kit and ligated with the pCANTAB6 vector digested with the same restriction enzymes. The DNA was electroporated into competent *E. coli* TG1 cells as described above and resulted in a done named p9A4ICAT7-1 (ATCC 98593) which contained an active scFv. The DNA sequence of this 9A4 scFv is set forth in the Sequence Listing as SEQ ID NO: 7, while the amino acid sequence is set forth separately as SEQ ID NO: 40. Note that the GTG codon, beginning at position 29 of SEQ ID NO: 7 is the start codon (Met). The sequencing oligos used were pUC19R and FDTETSEQ which are set forth in the Sequence Listing as SEQ ID NOS: 39 and 41 respectively.

See the information for SEQ ID NOS: 7 and 40 in the Sequence Listing for specific features of the DNA and amino acid sequences for this scFv antibody.

The genetically engineered 9A4 $V_H$-Linker-$V_L$ format scFv antibody was expressed in *E. coli* TG 1 cells, and the antibody was purified using NTA-Ni agarose (QIAgen) affinity chromatography, followed by Superdex 75 gel filtration chromatography to isolate monomer scFv species. The binding to the parental antigen of the scFv was evaluated on the BIAcore (see below). *E. coli* containing the plasmid pA4 1CAT7-1 has been deposited with the American Type Culture Collection as ATCC 98593.

Construction of 9A4 scFv ($V_L$-linker-$V_H$) in pATDFLAG

SOEing oligos were also prepared for PCR-SOE assembly of the $V_H$ and $V_L$ fragments in the opposite configuration, i.e. $V_L$-linker-$V_H$, relative to the example presented above in p9A4ICAT7-1. Two primers were designed for the $V_L$-linker region: at the 5' end an Nco I site was added and at the 3' end, an overlapping sequence with the 25 amino acid linker sequence set forth in the Sequence Listing as SEQ ID NO: 42 (Pantoliano M W, Bird R E, Johnson S, Asel E D, Dodd S W, Wood J F, and Hardman K D Biochemistry 1991; 30:10117–10125) was added. The 5'$V_L$ primer was named 9A4VL5ATD and the 3'$V_L$ primer was named 9A4VL3ATDILE. The sequences of these oligos are set forth in the Sequence Listing as SEQ ID NOS: 43 and 44 respectively.

For the $V_H$, a 5' end primer with overlap into the linker region and a 3' end PCR primer with an added Nhe I site was designed. The 5'$V_H$ primer was named 9A4VH5ATD and the 3'$V_H$ primer was named 9A4VH3ATD. The sequences of these oligos are set forth in the Sequence Listing as SEQ ID NOS: 45 and 46 respectively.

The $V_L$ and $V_H$ components were amplified by PCR. The $V_L$ and $V_H$ were then joined in the linker region, by a SOE-PCR using the oligos 9A4VL5ATD (SEQ ID NO: 44) and 9A4VH3ATD (SEQ ID NO: 46). DNA at the correct size, ca. 700 bp was excised out from a 1% agarose gel and eluted using the QIAquick gel elution kit. The resulting DNA was trimmed at the ends with the restriction enzymes Nco I at the 5' end and Nhe I at the 3' end. This was ligated with the expression vector pATDFLAG (PCT WO 93/12231) treated with the same restriction enzymes. Competent E. coli DH5α cells were transformed with the ligation as per the manufacturer's protocol and plated on agar plates containing 20 μg/mL of chloramphenicol as the selective agent. Two of the clones that were sequenced, p9A4IF-5 and p9A4IF-69, had no PCR or construction errors. The sequencing oligos were: UNIVLSEQ-5' (SEQ ID NO: 30) and TERMSEQ(-) (SEQ ID NO: 31).

E. coli containing p9A4IF-5 was chosen for further work and expression of the engineered 9A4 scFv antibody. The DNA sequence of this scFv is set forth in the Sequence Listing as SEQ ID NO: 8, while the derived amino acid sequence is set forth separately as SEQ ID NO: 47. Specific features of the $V_L$-L-$V_H$-FLAG 9A4 scFv, such as signal peptide, linker and tag locations are indicated in the Sequence Listing for SEQ ID NOS: 8 and 47. It will be obvious to those skilled in the art that the engineered antibody described could be expressed not just from E. coli, but from other organisms as well, including, but not limited to-P. pastoris, Baculovirus, Bacillus species, mammalian cells etc.

For expression and purification of this scFv product from E. coli, 1–2 L cultures of LB broth containing 20 μg/mL of chloramphenicol were grown overnight at 37° C. Cells were pelleted in a Sorvall centrifuge using a GS-3 rotor. In preparation for affinity chromatography using an M2 affinity column (Kodak, New Haven, Conn.) (which is specific for the FLAG epitope shown in the sequence above) the pelleted E. coli cells were processed either in a Tris/EDTA/sucrose media to isolate the periplasmic fraction or were sonicated (Soniprep sonicator) directly in a minimal volume of DPBS buffer. The affinity column was washed extensively with DPBS to remove any unbound materials after loading the crude scFv sample. The scFv antibody was eluted using 0.1 M glycine-HCl pH 3.1. The monomer scFv species was isolated by Superdex-75 gel filtration chromatography (Pharmacia). The antibody was judged to be homogeneous by SDS-PAGE and staining with Coomassie Brilliant Blue R-250. Antibody was quantitated spectrophotometrically at OD 280 nm, where an absorbance of 1.4 was defined to be equivalent to 1.0 mg/mL scFv, using a 1.0 cm pathlength quartz cuvette. E. coli containing the plasmid p9A4IF-5 was deposited with the American Type Culture Collection as ATCC-98592.

Binding to antigen was evaluated on the BIAcore for both the p9A4ICAT7-1 and p9A4IF-5 scFv purified gene products as follows. A streptavidin chip was loaded with biotinylated peptide of SEQ ID NO: 14 as given in Example 1 above. Both scFv constructs were shown to bind antigen, i.e., compared to the parent 9A4 IgG which binds with a K of $1.2 \times 10^{-7}$ M, the 9A4IF-5 scFv has a K of $1.1 \times 10^{-7}$ M. For the 9A4ICAT7-1 scFv, the off-rate was $1.2 \times 10^{-3}$ sec$^{-1}$ compared to $1.76 \times 10^{-2}$ sec$^{-1}$ for 9A4 IgG (parent antibody). These data indicate that the affinity of the engineered antibodies were at least as good or better than the parent.

As evidenced by the specificity and kinetic data determined by BIAcore, the 2 engineered antibodies containing the 9A4 $V_L$ and $V_H$ domains described above have the desired characteristics for using them in the quantitative measurement assays described in Examples 3 and 4 above.

Other engineered antibodies comprised of some or all of the 9A4 $V_L$ and $V_H$ disclosed herein having the affinity and specificity of the parent 9A4 antibody, would therefore be considered to be in the scope of claims for this invention.

EXAMPLE 7

Preparation of the Genetically Engineered Antibodies Related to 5109.

Before cloning the 5109 variable region genes, it was necessary to determine the protein sequence of portions of the variable domains of the parent 5109 antibody so that when the variable domains were cloned, it could be ascertained that the correct variable domains were indeed obtained and not other ones derived from the myeloma fusion partner or an inactive pseudogene from the B cell used in generating the hybridoma. Culture supernatant containing 5109 was generated by growing the 5109 hybridoma in roller bottles. Supernatants were adjusted to pH 7.5 with dibasic sodium phosphate and the salt concentration adjusted with 3 M sodium chloride to a final concentration of 150 mM. Filtered (0.2μ) supernatant was passed through a 15 mL bed volume of Protein G (Pharmacia) at a flow rate of 20 mL/min. After further washing the column with 150 mM NaCl solution, the antibody was eluted with 100 mM glycine pH 3.1. The antibody was isotyped using anti-sera from the Mouse Immunoglobulin Isotyping Kit (Boehringer Mannheim) and found to be an IgG1 class murine antibody with a kappa light chain constant domain.

In the present work, the heavy and light chains of MAb 5109 were separated by SDS-PAGE with the use of a reducing agent (beta-mercaptoethanol) in the sample buffer. Following electrophoresis, polypeptides in the gel were electroblotted to a PVDF membrane and detected by staining with Coomassie Brilliant Blue R-250. Bands containing the heavy and light chains of 5109 were then excised and subjected to Edman degradation. Sequencing was performed on a Perkin-Elmer Applied Biosystems Model 494 Procise protein sequencer as per the manufacturer's protocols. The sequences of the heavy and light chains that were obtained are shown in Table 9, and correspond to residues 1 to 40 of SEQ ID NO: 48 for the $V_H$ and to residues 1 to 39 of SEQ ID NO: 49 for the $V_L$.

TABLE 9

Results of N-terminal amino acid sequence of 5109.

| Res # | Heavy chain | Res # | Light chain |
|---|---|---|---|
| 1 | E | 1 | D |
| 2 | V | 2 | V |
| 3 | Q | 3 | V |
| 4 | L | 4 | M |
| 5 | V | 5 | T |
| 6 | E | 6 | Q |
| 7 | S | 7 | T |
| 8 | G | 8 | P |
| 9 | G | 9 | L |
| 10 | G | 10 | T |
| 11 | S | 11 | L |
| 12 | V | 12 | S |
| 13 | Q | 13 | V |
| 14 | P | 14 | T |
| 15 | G | 15 | I |
| 16 | G | 16 | G |
| 17 | S | 17 | Q |
| 18 | L | 18 | S |
| 19 | K | 19 | A |

TABLE 9-continued

Results of N-terminal amino acid sequence of 5109.

| Res # | Heavy chain | Res # | Light chain |
|---|---|---|---|
| 20 | L | 20 | S |
| 21 | S | 21 | I |
| 22 |   | 22 |   |
| 23 | A | 23 |   |
| 24 | A | 24 | K |
| 25 | S | 25 | S |
| 26 | G | 26 | S |
| 27 | F | 27 | Q |
| 28 | T | 28 |   |
| 29 | F | 29 | L |
| 30 | N | 30 | L |
| 31 | T | 31 | G |
| 32 | Y | 32 | (S) |
| 33 | G | 33 | D |
| 34 | M | 34 | (G) |
| 35 | S | 35 | L |
| 36 | W | 36 | T |
| 37 | V | 37 | Y |
| 38 | R | 38 | (L) |
| 39 | Q | 39 | I |
| 40 | T | 40 |   |

Cloning and Determination of the $V_L$ and $V_H$ Sequences of MAb 5109

The 5109 hybridoma cell line was grown in HT media (Sigma) with 5% fetal calf serum (Hyclone). Cells were pelleted ($2.5 \times 10^7$ cells/pellet) and frozen at −80° C. until use. Extraction of mRNA (Oligotex™ Direct mRNA Kit; QIAGEN) was carried out according to the manufacturer's directions. cDNA was then synthesized for the $V_L$ and $V_H$ regions using Boehringer Mannheim's First-Strand cDNA Synthesis Kit. The oligo used in the $V_L$ cDNA reaction was specific for the murine light chain kappa region (MLK) while the oligo used in the $V_H$ cDNA reaction, MHG, was specific for a segment in the murine heavy chain $C_H2$ gamma region. The sequences of oligos MLK and MHG are set forth in the Sequence Listing as SEQ ID NOS: 21 and 22, respectively.

PCR primers were designed for the N-terminal sequence of the mature, secreted forms of the heavy and light chains based on the amino acid sequences that were obtained for the $V_L$ and $V_H$ by Edman degradation. The sequences were compared with the Kabat database; the 5109 $V_H$ was found to be most similar to members of Kabat subgroup IIID, while the 5109 $V_L$ was most similar to members of Kabat subgroup II.

The sequences of the 5'$V_H$ primer and 5'$V_L$ primer were named 51-09$V_H$5'NDe and 51-09$V_L$5'NDe respectively, and are set forth in the Sequence Listing as SEQ ID NOS: 50 and 51.

Reverse primers were designed from known sequences of the IgG1 heavy chain constant region (to a segment in the $C_H1$ domain) and the constant region of the kappa light chain. Both of these 3' oligos are 5' (upstream) of the original oligos used to generate the cDNA. The 3'$V_H$ primer, named MIGG1CH1 and the 3'$V_L$ primer named MULK2 are set forth in the Sequence Listing as SEQ ID NOS: 28 and 52, respectively.

The resulting PCR products for the $V_L$ and $V_H$ were ligated into pCR2.1 and representative clones were chosen for subsequent DNA sequencing. DNA sequencing was performed on an Applied Biosystems Model 373 Stretch Sequencer and was set up and operated according to the protocols provided by the vendor. For DNA sequence determination, the Invitrogen commercial sequencing oligos M13F and M13R were used, the sequences of which are set forth in the Sequence Listing as SEQ ID NOS: 53 and 54.

The first 21 amino acids that were determined by Edman degradation for the 5109 $V_L$ and $V_H$ mature amino termini were found to be identical to the corresponding amino acid sequences derived from the DNA sequence of the corresponding genes that were cloned here by PCR.

The DNA sequences of the 5109 $V_H$ and $V_L$ domains are set forth in the Sequence Listing as SEQ ID NOS: 10 and 11, respectively. The amino acid sequences of the 5109 $V_H$ and $V_L$ are set forth separately in the Sequence Listing as SEQ ID NOS: 48 and 49, respectively. It should be noted that while the DNA, as presented, codes for the correct amino acids in the amino terminal segments of each of the $V_L$ and $V_H$ seqments corresponding to the PCR annealing oligos, the exact codons for the antibody amino acid segments corresponding to these oligos, as they would have occurred in the original hybridoma DNA are not unequivocal. The 5109 $V_H$ utilized the $J_H3$ joining segment gene with 2 mutations in the codon that would otherwise code for a Thr residue (positions 328 and 330 of SEQ ID NO: 10), but in the 5109 $V_H$ is an Ala residue (position 110 of SEQ ID NO: 48).

The 5109 variable heavy chain is most related to Kabat's Mouse Ig heavy chain Family XIV and most closely resembles Database ID number 002754. There are 24 nucleotide differences between these 2 $V_H$ genes, resulting in 14 amino acid differences. It is most likely, based on this high number of differences, that these two genes are not derived from the same germline gene. It is still possible, however, that the 2 are derived from the same germline and that both have been heavily mutated in the in vivo affinity maturation process and the resulting divergence was amplified.

We claim $V_H$ genes in other antibodies related to the 5109 $V_H$ germline gene, such that when the $V_H$ gene product forms a productive antibody $V_L$-$V_H$ pair with the $V_L$ of this other antibody, it binds in a manner (specificity and affinity) analogous to 5109.

The 5109 $V_L$ utilized a J5 joining segment and codes for amino acids 102 to 112 of SEQ ID NO: 49. The CDR3 for this antibody is relatively rare because of the Cys-94 residue contained therein. The CDR3 extends from residues 94 to 102 of SEQ ID NO: 49. When 5109 single chain antibodies were engineered with a 5109 $V_L$ (see below) 2 versions were made, one with the parental Cys-94 and another with Ser substituting the Cys-94.

The 5109 $V_L$ belongs to Kabat's Mouse Kappa Family VI and is most similar to Database ID Numbers 005841, 005842, 005843, and 005844. The 4 antibodies in the database are identical in their nucleotide sequences, so a comparison with the 5109 $V_L$ can be made to all 4 of them at the same time. There are 12 nucleotide mismatches, resulting in 8 amino acid differences. One of these differences occur in FR1, 3 in CDR1, 1 in FR2, 1 in CDR2, 1 in FR3 and 1 in CDR3. These changes occur throughout the $V_L$, but are focused on the CDRs, with 5 out of the 8 differences being in these hypervariable segments. Therefore it is most likely that these genes are related by being derived from the same or at least very similar germine $V_L$.

We claim $V_L$ genes in other antibodies related to the 5109 $V_L$ germline gene, such that when the $V_L$ gene product forms a productive antibody $V_L$-$V_H$ pair with the $V_H$ of this other antibody, it binds in a manner (specificity and affinity) analogous to 5109.

We also claim antibodies where both the $V_L$ and $V_H$ are derived from the 5109 $V_L$ and $V_H$ germline genes, disclosed in this patent, such that when the $V_L$ and $V_H$ gene products form a productive $V_L$-$V_H$ pair, this other or different antibody from 5109 essentially binds in a manner (specificity and affinity) analogous to 5109.

Construction of 5109 scFv Engineered Antibody ($V_H$-Linker-$V_L$) in pUC119

SOEing (Splicing by Overlap Extension) PCR primers were utilized to prepare for assembly of the $V_H$ and $V_L$ components. All of the oligos utilized in 5109 scFv construction were synthesized in-house using a Beckman Oligo 1000M DNA synthesizer (Fullerton, Calif.). These five PCR primers, called 5109 VH5', 5109 VH3', 5109 VL5', 5109 VL3'SER and 5109 VL3'CYS are set forth in the Sequence Listing as SEQ ID NOS: 55, 56, 57, 58 and 59 respectively.

The oligo 5109 VL3'Ser (SEQ ID NO: 58) was used to change Cys-94 of SEQ ID NO: 49 to Ser-94 in the scFv construct, (corresponds to the Cys residue at position 248 of SEQ ID NO: 63) to potentially improve the stability of the resulting scFv. Another primer, 5109 VL3'Cys (SEQ ID NO: 59) was also synthesized in order to retain the original Cys sequence.

Following the SOEing reaction, DNA was amplified by PCR and the product sequenced directly for sequence confirmation.

DNA sequence was verified using an Applied Biosystems Model 373 Stretch Sequencing Unit as per the directions of the manufacturer. The following oligos were used for sequencing of potential 5109 scFv engineered antibodies ligated directly into pUC119: pUC19R, MycSeq10, Gly4Ser5', Gly4Ser3', the sequences of which are set forth in the Sequence Listing as SEQ ID NOS: 39, 60, 61 and 62, respectively.

For those 5109 DNA cassettes ligated into the pCR2.1 vector, the M13F and M13R oligos purchased from InVitrogen (SEQ ID NOS: 52 and 53) were utilized for sequence priming reactions, along with SEQ ID NOS: 61 and 62, as two internal oligos.

Clones directly ligated into pUC119 contained a large number of PCR errors. An acceptable clone (H55) was identified however, in the pCR2.1 vector. This construct was then subcloned by digesting the scFv with Sfi I and Not I and ligated in the pUC119 vector similarly digested. Clones were screened for insert by PCR amplification using pUC19R and MycSeq10 oligos (SEQ ID NOS: 39 and 60). Three clones were submitted for sequencing. One clone was identified with the desired sequence and is designated p5109CscFv7 (ATCC 98594); the DNA and derived amino acid sequences are set forth in the Sequence Listing as SEQ ID NOS: 9 and 63, respectively. Sequence features of this engineered antibody are given in SEQ ID NO: 63. In generating the 5109 scFv by PCR, a mutation (PCR error) occured at nucleotide 738 of SEQ ID NO: 9, changing the amino acid coded for by the altered codon from valine to alanine. This corresponds to the Ala residue at position 237 of SEQ ID NO: 63 (the 5109 scFv sequence). As a conservative difference, it was considered unimportant in terms of affecting the activity of genetically engineered products and was thus allowed to be carried forward in the $V_L$ of the scFv constructs described. Of course, for those skilled in the art, it will be apparent that this PCR error could also be corrected and the original Val residue obtained at this position.

To verify that the new single chain constructs retained the binding properties of the parent molecule, the 5109 scFv was expressed in E. coli and purified.

A 2YT starter culture (50 mL) containing 100 ug/mL ampicillin and 2% glucose was inoculated with 50 uL of −80° C. glycerol stock. Cultures were incubated ON at 30° C. with shaking at 300 rpm. Each of six 2 L flasks containing 2YT media supplemented with 100 μg/mL ampicillin and 0.1% glucose were inoculated with 5 mL of the overnight starter culture. Cultures were incubated 30° C. until turbid and subsequently induced by adding IPTG isopropyl B-D-thiogalactopyramoside (Boehringer Mannheim) to a final concentration of 1 mM. Cultures were grown for an additional 4 hr for production of scFv. Cells were centrifuged at 5000×g for 10 min. Cell pellets were stored at −20° C. until processed.

For scFv purification, cell pellets were resuspended in TES (0.2 M Tris-HCl, 0.5 mM EDTA, 0.5 M sucrose). Following resuspension, a 1:5 dilution of the above TES buffer containing protease inhibitors (Complete Protease Inhibitor Cocktail, Boehringer Mannheim) was added. This preparation was allowed to incubate at 4° C. for 30 min. Following incubation, cells were pelleted at 12,000×g for 15 min. $MgCl_2$ was added to the resulting supernatant to a final concentration of 5 mM. Ni-NTA agarose (QIAgen) was washed 1× in PBS containing 300 mM NaCl, 15 mM imidazole, 0.2% Triton-X, pH 7.4. Washed agarose was then added and the slurry was allowed to incubate for 30 min at 4° C. Ni-NTA agarose beads+scFv were then washed 4× as previously described. The scFv was then eluted in wash buffer containing 250 mM imidazole. The eluate was desalted over a NAP-25 column (Pharmacia-Biotech, Uppsala, Sweden) and concentrated using a Centriprep concentrator device (Amicon, Beverly, Mass.). Products were electrophoresed on SDS-PAGE and visualized by silver staining. The resulting scFv products for p5109CscFv7 (Cys) and p5109SscFvA9 (Ser) were approximately 15% and 75% pure, respectively.

Using Origen methodology (Technical manual, Origen Instrument, Igen Corporation, Gaithersburg, Md.), binding to biotinylated peptide 225 (having the sequence set forth in the Sequence Listing as SEQ ID NO: 64) by the 5109 scFv species was measured. Peptide 225 was prepared by Anaspec. Peptide 225 was added to 800 μg/mL streptavidin coated magnetic beads (Dynabeads, Igen, Gaithersburg, Md.) to bring the final concentration to 10 nM and incubated for 15 minutes. The new genetically engineered scFv antibody was added to the peptide/bead solution for 30 min with shaking. The 9E10 anti-myc tag ruthenylated MAb was added in 200 μL Igen assay buffer (Igen, Gaithersburg, Md.) and the ECL signal read on the Origen Instrument (Igen). MAb 9E10 was generated and purified from the 9E10 cell line, which was obtained from the ATCC. The MAb was ruthenylated using the N-hydroxysuccinamide derivative Origen TAG-NHS Ester (Igen) according to the manufacturer's instructions. In the absence of 5109 scFv, a background signal of 2995 ECL units was obtained. Addition of the 5109 scFv Cys construct (p5109CscFv7) resulted in 536,997 ECL units. Addition of the 5109 scFv Ser construct (p5109SscFvA9) resulted in 694,253 ECL units. These results demonstrate that both 5109 scFv genetically engineered antibodies were biologically active and bound to the same collagen-related peptide fragment as MAb 5109 does. A culture of E. coli containing p5109CscFvA9 was deposited with the American Type Culture Collection as ATCC-98594.

The specificity data determined by the Origen technology demonstrates that the engineered antibody containing the 5109 $V_L$ and $V_H$ domains described above have the desired characteristics for using it in the quantitative measurement assays described in Examples 3 and 4 above. Other engineered antibodies comprised of some or all of the 5109 $V_L$ and $V_H$ disclosed here, having the affinity and specificity of the parent 5109 antibody would therefore be considered to be in the scope of claims for this invention.

It should also be noted that engineered antibodies comprised of a combination of the 9A4 and 5109 $V_L$ and $V_H$ domains, such as a bispecific scFv dimer of the composition: 5109$V_L$-Linker-5109$V_H$-Linker-9A4$V_L$-Linker-9A4$V_H$-Tag(s) would also be useful, as the only antibody reagent in Examples 3 and 4 above. The difference would be that a single bispecific reagent could be used in a one step ELISA rather than using 9A4 and 5109 separately. To those skilled in the art, it is obvious that a number of genetic compositions comprising the subject antibodies' variable domains could be joined to make a variety of bispecific molecules and thus simplify the assays presented in Examples 3 and 4. The avidity of such molecules could be such that the overall sensitivity of the assay may also be significantly improved.

EXAMPLE 8

Mutations or differences in amino acid sequences of antibodies related to the subject invention antibodies can retain the binding properties (affinity and specificity) and therefore the utility of the parent antibody. This is demonstrated below by generating a series of mutants in the CDR3 of the 9A4 $V_H$. To those skilled in the art, it is apparent that other mutations in other regions of the same germline $V_L$ and $V_H$ genes of both 9A4 and 5109 can give antibodies of the same or of better binding properties relative to the original antibodies disclosed in this invention.

Generation of 9A4 VH CDR3 Region Mutants

The pCANTAB6 derivative of the 9A4 scFv, namely p9A4ICAT7-1 presented in Example 6 above, was used as the starting material to generate mutants in the CDR3 segment and the Vernier residues immediately adjacent to the CDR3. The parent DNA sequence of the CDR3 $V_H$ region being targeted for mutation comprised nucleotides 383 to 409 of SEQ ID NO: 7. The derived amino acids corresponding to these nucleotides are residues 119 to 127 of SEQ ID NO: 40. The CDR3 begins at residue 121 and ends at 126. To introduce the random mutations in this area, the $V_H$ and $V_L$ regions were amplified separately by 2 PCRs. In the first PCR, oligos (obtained from Oligos Etc.) pUC19R (SEQ ID NO: 39) and 9A4MUT (set forth in the Sequence Listing as SEQ ID NO: 65) were used to amplify the $V_H$ portion, where 9A4MUT was the oligo which introduced the mutations.

Nucleotides 25 to 51 in 9A4MUT (SEQ ID NO: 65) were 10% spiked. In other words, the sequence as written accounted for 90% of the nucleotide added at each position 25–51, while the other 3 nucleotides, in each position, 25 through 51, were introduced to the growing oligo chain at 3.3% each. This was accomplished by methods well known in the art of oligonucleotide synthesis. The fact that random nucleotides were indeed introduced in this defined region will be discussed below. The second PCR utilized the 2 oligos: (also obtained from Oligos Etc) 9A4L5 (SEQ ID NO: 66) and FDTETSEQ (SEQ ID NO: 41). This produced the Linker-$V_L$ portion up to the Not I site in p9A4ICAT7-1 at the 3' end and with overlap into the $V_H$ at the 5' end that would allow subsequent annealing and assembly with the mutated $V_H$ PCR products from the first PCR.

The PCR was set up as follows. For the mutant $V_H$, 50 pmol of each of the oligos pUC19R (SEQ ID NO: 39) and 9A4MUT (SEQ ID NO: 65) were used in 100 microliter reactions. The template DNA target was an aliquot of SNAP (Invitrogen) purified plasmid DNA-p9A4ICAT7-1. Taq Polymerase (Perkin Elmer) was used in the 30 cycle PCR. Denaturation, annealing and polymerase reaction times and temperatures were 94° C. for 1 min, 55° C. for 1 min and 72° C. for 2 min, respectively.

For the 30$^{th}$ cycle the polymerization reaction was extended for a total of 10 min, before cooling the reaction to 4° C. For the $V_L$, which would overlap with the $V_H$ spedes, PCRs were set up using both KlenTaq polymerase (Clontech) and Taq Polymerase (Perkin Elmer). DNA products were purified with the QIAgen gel extraction kit. The PCR assembly reaction for the mutated $V_H$ and the $V_L$ was performed using aliquots (1–2 microliters) of each of the purified PCR products in a 25 cycle total/2 temperature cycling. 94° C. for 1 min, 65° C. for 4 min and holding at 4° C. at the end. No oligos were used for this step. For the PCR pull-through of the mutated 9A4 assemblies, 5 microliters of unpurified assembly reaction was used as the template and the oligos pUC19R (SEQ ID NO: 39) and FDTETSEQ (SEQ ID NO: 41) as the annealing primers. Correct size products were observed at ca. 900 bp and were gel purified using the QIAgen gel extraction kit. The mutated 9A4 scFv inserts were treated with Sfi I and Not I to prepare for ligation with the pCANTAB6 vector DNA cut with the same restriction enzymes. After ligation, the DNA mixture was ethanol precipitated and dissolved in 24 microliters of sterile deionized distilled water. Preparation of competent *E. coli* TG1 cells and electroporation was conducted as described in Example 6. Twelve separate electroporations were performed and ultimately pooled and plated. A total of 1.5×10$^6$ clones were obtained and stored as a glycerol stock at –80° C. A random sampling of 12 clones indicated that 9 of them (one clone failed to give sequence data) had an insert when screened by PCR, using the oligos FDTETSEQ (SEQ ID NO: 41) and pUC19R (SEQ ID NO: 39). These inserts were purified using the QIAgen kit and the sequence in the CDR3 $V_H$ determined. The results of the sequencing data are presented below. The DNA sequence of the "Parent Sequence" is set forth in the Sequence Listing as nucleotides 383 to 409 of SEQ ID NO: 7.

|  |  | Number of Mutations |
|---|---|---|
| Parent Sequence: | 5'- GCT AGG GGC GGT AGC CTT GAC TAC TGG -3' | — |
| 9A4MUT-1: | 5'- GCT CGG GGC GGT AGC CTT GAC TAC CGG -3' | 2 |
| 9A4MUT-3: | 5'- GCT GGG CCC TGT ATC CTT GAT TAC TGG -3' | 6 |

```
                                                         Number of
                                                         Mutations

9A4MUT-4:      5'- GCT ACG GGA GGT AGC CTT GAC TAC TGG -3'      2

9A4MUT-6:      5'- GTT TGG GGC GGC AGC CCT GAC CAC AGG -3'      6

9A4MUT-7:      5'- GCT TGG GGC GGC AGG TAT GAC TAC TGG -3'      5

9A4MUT-8:      5'- GCT ANG GTC AGT AGC CTT GAC TCC TGG -3'      3

9A4MUT-10:     5'- GCT ACG GGC TGT AGT CAT GAC TAC CGC -3'      6

9A4MUT-12:     5'- GCT AGG GGT GGT AGC CTT GAC TAC TGG -3'      1
```

The mutations in the cohort above vary in number from 1 to 6 for each clone, and they occur at various positions. The mutations are indicated in bold underline in the various clones above N=nucleotide could not be assigned. Only 1 clone (9A4MUT-12) out of 8, checked in this random manner, gave parent amino acid sequence. Based on the randomness of the results shown above, a good mutated library was generated. Therefore, a biotin selection was performed to find binders to peptide 040 (SEQ ID NO: 14) which is the epitope for 9A4.

Description of Biotin Selection for Antibodies Obtained Below

An aliquot of approximately 100 μL of mutated library stock was added to 25 mL of 2YT media containing 100 μg/mL ampicillin and 2% glucose. The culture was incubated at 37° C. for approximately 60 min or until cells reached mid-log phase ($OD_{600\ nm}$=0.5 to 1.0). M13K07 helper phage (Pharmacia, Uppsala, Sweden) was then added to the culture to a concentration of $5 \times 10^8$ pfu/mL. The helper phage were then allowed to infect the culture for 20 min at 37° C. without shaking and then for another 25 min at 37° C. with shaking at 200 rpm. The infected cells were transferred to a 50 mL conical centrifuge tube and pelleted at 3000 rpm for 10 min. Cells were resuspended in 2YT media containing 100 μg/mL ampicillin and 50 μg/mL kanamycin. This culture was transferred to a fresh 250 mL flask and incubated at 30° C. for 2 h during which time phage particles were produced. Cells were removed by centrifugation at 14,000 rpm for 2 min. Aliquots (1 mL) of phage were then blocked for 30 min at room temperature by the addition of PBS and NFDM to a final concentration of 1× PBS and 3% NFDM. This was accomplished by the addition of 200 μL of a 6× PBS, 18% NFDM solution to 1 mL of phage. Biotinylated peptide 040 (SEQ ID NO: 14) was added to the phage solution at concentrations ranging from 10 pM to 1 μM. This solution was incubated for 60 min at RT. Streptavidin-coated magnetic beads (Dynal, Oslo, Norway) were blocked at RT with end-over-end shaking in 3% NFDM in PBS. Following incubation, the streptavidin beads were captured at the side of the tube with a magnet and the blocking solution carefully aspirated away. The blocked phage with the bound peptide was then added to the streptavidin beads and allowed to incubate at RT with end-over-end shaking for 15 min. Bead complexes were captured magnetically and unbound phage carefully aspirated away. Magnetic bound bead complexes were washed 4× with PBS containing 0.1% TW-20 and 4× with PBS alone. Following the final capture, bead complexes were resuspended in 100 μL of 100 mM triethylamine in PBS and neutralized with an equal volume of 1 M Tris pH 7.4. Mid-log phase *E. coli* TG1 cells (10 mL) were then infected with 100 μL of bead complexes. Infection was allowed to progress for 20 min at 37° C. without shaking and then for another 25 min at 37° C. with shaking at 200 rpm. Infected cells were then pelleted, resuspended in 500 μL of fresh 2YT media and 500 μL plated onto 243×243 mm 2YT agar plates containing 100 μg/mL ampicillin and 2% glucose. Plates were incubated overnight at 30° C. Following approximately 16 h of growth, the colonies were recovered by scraping and used to inoculate liquid cultures. The process was repeated for a minimum of two and a maximum of five rounds of selection.

Clones recovered from the biotin selection were grown, induced for production of scFv, which was purified according to the protocol outlined below.

Preparation of scFv Mutant Clones Using Hypotonic Shock Method

The culture were pelleted and resuspended in 0.8 mL ice cold TES buffer (0.2 M Tris-HCl, 0.5 nM EDTA, 0.5 M sucrose). TES (1.2 mL of ice cold 1:5 dilution) was added and the culture was incubated on ice for 30 min. The cells were pelleted at 4° C. at 14,000 rpm (30 min). The scFv supernatant was added to a fresh tube containing 10 μL of 1.0 M $MgCl_2$. NTA-agarose (200 μL) (QIAgen) was prepared by washing in a phosphate imidazole wash buffer containing 50 mM Na phosphate, pH 8.0, 500 mM NaCl, 20 mM imidazole and 0.1% TW-20. The scFv supernatant was added to the NTA-agarose and incubated at 4° C. for approximately 30 min. The NTA-agarose with scFv was spun and 500 volumes of elution buffer was added. The elution buffer consisted of 50 mM Na phosphate, pH 8.0, 500 mM NaCl and 250 mM imidazole. The eluate was vortexed and centrifuged to remove the NTA-agarose. The scFv supernatant was buffer exchanged by passing it over a NAP-5 column (Pharmacia), according to the manufacturer's instructions.

Measurement of Off-rates for scFv Constructs

Off-rates for the scFv constructs were measured by analysis of dissociation data obtained on the BIAcore (Pharmacia Biosensor) with BIAevaluation ver 2.1 software. To obtain the data on the BIAcore, streptavidin surfaces on the BIAcore chips were prepared as described previously in Example 1. Biotinylated peptide (SEQ ID NO: 14) was bound to the prepared streptavidin surfaces to RU densities ranging from about 2–11 RU's/surface. The lower level of derivatization would help avoid getting erroneous off-rates that could be obtained if mass transport was an issue. Purified scFv's were injected over these surfaces to allow binding of the constructs for 60 seconds. PBS buffer alone was then substituted and the dissociation of scFv was allowed to proceed for an additional 280 sec. Off-rates were calculated from these dissociation data.

TABLE 10

Summary of 9A4 CDR3 $V_H$ Mutant Sequences
Amino acid sequences determined from the results of DNA sequencing. The parent sequence for clone ICAT7-1 corresponds to residues 118 to 127 or SEQ ID NO: 40.

| Clone | Sequence | | | | | | | | | | off-rate × $10^{-2}$ sec$^{-1}$ |
|---|---|---|---|---|---|---|---|---|---|---|---|
| ICAT7-1 | C | A | R | G | G | S | L | D | Y | W | 0.3 |
| 15A | C | A | R | G | G | R | L | D | Y | W | 0.35 |
| 16A | C | X | R | G | G | S | L | D | L | L | 0.26 |
| 23A | C | G | R | G | R | S | L | D | Y | X | 0.26 |
| 24A | C | G | R | G | G | S | L | E | Y | W | 0.25 |
| 26A | X | X | R | G | X | S | X | E | Y | L | 0.27 |
| 28A | X | X | R | G | T | X | E | Y | X | | 0.3 |
| 9B | C | X | R | G | G | S | F | E | Y | W | 0.32 |
| 13B | C | X | R | G | G | S | X | D | F | W | 0.26 |
| 14B | C | A | R | G | G | S | L | D | H | W | 0.27 |
| 20B | C | G | R | G | G | N | L | D | H | C | 0.28 |
| 26B | C | G | R | G | X | T | L | E | F | W | 0.34 |
| 31B | C | G | R | G | G | S | L | D | Q | X | 0.26 |
| 37B | C | G | R | G | G | T | L | D | X | X | 0.33 |
| 38B | C | G | R | G | G | S | L | D | S | C | 0.26 |
| 2C | C | G | R | G | S | S | X | D | Y | C | 0.28 |
| 5C | C | A | R | G | G | S | L | D | S | W | 0.25 |
| 9C | C | X | R | G | S | S | L | D | Y | X | 0.99 |
| 10C | C | G | R | G | G | S | L | D | Y | C | 0.94 |
| 20C | C | G | R | X | G | S | X | X | F | C | 1.29 |
| 26C | C | X | R | G | X | S | L | D | I | X | 0.95 |
| 29C | C | G | R | G | G | S | F | X | X | W | 1.04 |
| 8D | C | A | R | G | G | S | L | D | N | W | 1.04 |
| 16D | C | X | R | G | G | T | L | D | Y | W | 1.14 |
| 17D | C | X | X | G | R | S | L | E | X | W | 1.07 |
| 20D | C | X | R | G | X | T | L | X | Y | W | 1.02 |
| 18E | C | A | R | G | G | S | L | D | V | W | 1.4 |
| 13G | C | G | R | G | G | S | L | D | N | W | 1.03 |
| 17G | C | X | R | G | G | S | L | D | F | W | 1.03 |
| 1H | C | X | R | G | G | S | L | D | H | W | 1.17 |
| 4H | C | X | R | G | G | S | L | X | V | W | 1.03 |
| 1J | C | A | R | G | G | X | I | D | V | W | 1.09 |
| IF-5 | C | A | R | G | G | S | L | D | Y | W | 0.48 |

Note: Clones ICAT 7-1 and IF-5 above show CDR3 regions having the parent sequence.

It is apparent from the data presented above that changes can be made in the amino acid sequence of the parent antibody while still retaining binding to the target. While differences in the off-rate of the antibodies presented above are within an order of magnitude, by targeting different regions of the antibody $V^H$ or $V_L$ for mutation, or finding different antibodies obtained by immunization which have $V_L$ and/or $V_H$ domains derived from the same germLine $V_L$ and $V_H$ genes as 9A4 or 5109, one may discover antibodies with variable or enhanced binding properties relative to the parental antibodies disclosed in Examples 6 and 7 cited above.

We claim:

1. A method for monitoring biological media for protein fragments which comprises;

contacting said biological media with a capture antibody; said capture antibody being active against the sequences set forth in the Sequence Listing as SEQ ID NOS: 1 and 2; and contacting said biological media with a detection antibody; said capture antibody being active against the sequences set forth in the Sequence Listing as SEQ ID NOS: 3 and 4; and detecting the amount of collagen fragments bound to said capture and detection antibodies; or contacting said biological media with a capture antibody; said capture antibody being active against the sequences set forth in the Sequence Listing as SEQ ID NOS: 3 and 4; and contacting said biological media with a detection antibody; said detection antibody being active against the sequences set forth in the Sequence Listing as SEQ ID NOS: 1 and 2; and detecting the amount of collagen fragments bound to said capture and detection antibodies.

2. A method of claim 1 wherein said protein fragments are collagen fragments generated by collagenase cleavage of articular cartilage.

3. A method of claim 2 wherein said protein fragments are generated from collagenase cleavage of type II collagen.

4. A method of claim 2 wherein said capture and detection antibodies are monoclonal antibodies.

5. A method of claim 1 wherein said capture and detection antibodies are monoclonal antibodies.

6. A method of claim 1 wherein said capture antibody is a genetically engineered antibody.

7. A method of claim 1 wherein said detection antibody is a genetically engineered antibody.

8. A method of claim 1 wherein said capture antibody, designated 9A4, has the $V_H$ sequence as set forth in the Sequence Listing as SEQ ID NOS: 5 and 32 and the $V_L$ sequence as set forth in the Sequence Listing as SEQ ID NOS: 6 and 33.

9. A method of claim 1 wherein said detection antibody, designated 5109, has the $V_H$ sequence as set forth in the Sequence Listing as SEQ ID NOS: 10 and 48 and the $V_L$ sequence as set forth in the Sequence Listing as SEQ ID NOS: 11 and 49.

10. An antibody of claim 1 which is labeled to facilitate detection.

11. An antibody of claim 10 wherein said label is radioactive, optical, enzymatic, fluorescent polarizing or fluorescent quenching.

12. An antibody of claim 1 which is labeled to facilitate capture of said antibody.

13. An antibody of claim 12 wherein said label is biotin or magnetic particles.

14. A method for monitoring biological media for protein fragments which comprises;

contacting said biological media with an antibody active against the sequences set forth in the Sequence Listing as SEQ ID NOS: 3 and 4; and detecting the amount of protein fragments bound to said antibody.

15. A method of claim 14 wherein said protein fragments are collagen fragments.

16. A method of claim 14 wherein said antibody is a monoclonal antibody.

17. A method of claim 14 wherein said antibody is a genetically engineered antibody.

18. A method of claim 14 wherein said antibody, designated 5109, has the $V_H$ sequence as set forth in the Sequence Listing as SEQ ID NOS: 10 and 48 and the $V_L$ sequence as set forth in the Sequence Listing as SEQ ID NOS: 11 and 49.

19. The antibody, designated 9A4, having the $V_H$ sequence as set forth in the Sequence Listing as SEQ ID NOS: 5 and 32 and the $V_L$ sequence as set forth in the Sequence Listing as SEQ ID NOS: 6 and 33.

20. The antibody, designated 5109, having the $V_H$ sequence as set forth in the Sequence Listing as SEQ ID NOS: 10 and 48 and the $V_L$ sequence as set forth in the Sequence Listing as SEQ ID NOS: 11 and 49.

21. A cell line that produces a specific binding partner that binds to peptides consisting essentially of the structures as set forth in the Sequence Listing as SEQ ID NOS: 1 or 2 wherein the cell line is ATCC HB-12436.

22. A cell line that produces a specific binding partner that binds to peptides consisting essentially of the structures as set forth in the Sequence Listing as SEQ ID NOS: 3 or 4 wherein the cell line is ATCC HB-12435.

23. A genetically engineered form of antibody 9A4 such as that expressed by E. coli p9A4ICAT7-1 or p9A4IF-5 deposited as ATCC-98593 and ATCC-98592, respectively.

24. A genetically engineered form of antibody 5109 such as that derived from E. coli p5109CscFv7, which may be substituted for 5109 deposited as ATCC-98594.

* * * * *

SEQUENCE LISTING

<160> NUMBER OF SEQ ID NOS: 69

<210> SEQ ID NO 1
<211> LENGTH: 7
<212> TYPE: PRT
<213> ORGANISM: Homo sapiens
<220> FEATURE:
<221> NAME/KEY: DOMAIN
<222> LOCATION: (1)..(7)
<223> OTHER INFORMATION: Type II Collagen Fragment

<400> SEQUENCE: 1

Gly Pro Pro Gly Pro Gln Gly
 1               5

<210> SEQ ID NO 2
<211> LENGTH: 7
<212> TYPE: PRT
<213> ORGANISM: Homo sapiens
<220> FEATURE:
<221> NAME/KEY: MOD_RES
<222> LOCATION: (3)
<223> OTHER INFORMATION: Type II Collagen Fragment with 4Hyp

<400> SEQUENCE: 2

Gly Pro Xaa Gly Pro Gln Gly
 1               5

<210> SEQ ID NO 3

```
<211> LENGTH: 10
<212> TYPE: PRT
<213> ORGANISM: Homo sapiens
<220> FEATURE:
<221> NAME/KEY: DOMAIN
<222> LOCATION: (1)..(10)
<223> OTHER INFORMATION: Type II Collagen Fragment

<400> SEQUENCE: 3

Gly Glu Pro Gly Asp Asp Gly Pro Ser Gly
 1               5                  10

<210> SEQ ID NO 4
<211> LENGTH: 10
<212> TYPE: PRT
<213> ORGANISM: Homo sapiens
<220> FEATURE:
<221> NAME/KEY: MOD_RES
<222> LOCATION: (3)
<223> OTHER INFORMATION: Type II Collagen Fragment with 4Hyp

<400> SEQUENCE: 4

Gly Glu Xaa Gly Asp Asp Gly Pro Ser Gly
 1               5                  10

<210> SEQ ID NO 5
<211> LENGTH: 408
<212> TYPE: DNA
<213> ORGANISM: Mus musculus
<220> FEATURE:
<221> NAME/KEY: sig_peptide
<222> LOCATION: (1)..(33)
<223> OTHER INFORMATION: Corresponds to portion of 9A4 heavy chain
      signal peptide.
<220> FEATURE:
<221> NAME/KEY: V_region
<222> LOCATION: (34)..(378)
<223> OTHER INFORMATION: Mature 9A4 heavy chain sequence after cleavage
      of signal peptide.
<220> FEATURE:
<221> NAME/KEY: C_region
<222> LOCATION: (379)..(408)
<223> OTHER INFORMATION: Portion of murine IgG1 CH1 sequence.

<400> SEQUENCE: 5
ttcctgatgg cagctgccca agtatccaa gcacagatcc agttggtgca gtctggtcct      60
gagctgaaga agcctggaga gacagtcaag atctcctgca aggcttctgg ttataccttc    120
acagactatt caatacactg ggtgaagcag gctccaggaa agggtttaaa gtggatgggc    180
tggataaaca ctgagactgg tgagccaaca tatgcagatg acttcaaggg acggtttgcc    240
ttctctttgg aaacctctgc cagcactgcc tatttgcaga tcaacaacct caaaaatgag    300
gacacggcta catatttctg tgctaggggc ggtagccttg actactgggg ccaaggcacc    360
actctcacag tctcctcagc caaaacgaca cccccatctg tctatcca                408

<210> SEQ ID NO 6
<211> LENGTH: 359
<212> TYPE: DNA
<213> ORGANISM: Mus musculus
<220> FEATURE:
<221> NAME/KEY: sig_peptide
<222> LOCATION: (1)..(23)
<223> OTHER INFORMATION: Portion of 9A4 VL signal peptide.
<220> FEATURE:
<221> NAME/KEY: V_region
<222> LOCATION: (24)..(341)
<223> OTHER INFORMATION: Mature 9A4 VL.
<220> FEATURE:
<221> NAME/KEY: C_region
```

<222> LOCATION: (342)..(359)
<223> OTHER INFORMATION: Portion of murine C kappa constant region.

<400> SEQUENCE: 6
cctcagtcat actgtccaga ggacaaattg ttctcaccca gtctccagta ttcatgtctg    60
catctccagg ggagaaggtc accatgacct gcagtgccag ctcaagtgta agttacatgt   120
actggtacca gcagaagcca ggatcctccc ccagactcct gattcatgcc acatccaacc   180
tggcttctgg agtccctgtt cgcttcagtg gcggtgggtc tgggacctct tactctctca   240
caatcagccg aatggaggct gaagatgctg ccacttatta ctgtcagcag tggagaagtt   300
atacacggac gttcggtgga ggcaccaagc tggaaatcat acgggctgat gctgcacca    359

<210> SEQ ID NO 7
<211> LENGTH: 883
<212> TYPE: DNA
<213> ORGANISM: Artificial Sequence
<220> FEATURE:
<223> OTHER INFORMATION: Description of Artificial Sequence: 9A4 single
      chain antibody, VH - VL.
<220> FEATURE:
<221> NAME/KEY: sig_peptide
<222> LOCATION: (29)..(94)
<223> OTHER INFORMATION: Engineered signal peptide in pCANTAB6;
      initiator methionine is coded for most likely by gtg codon.
<220> FEATURE:
<221> NAME/KEY: mat_peptide
<222> LOCATION: (95)..(880)
<223> OTHER INFORMATION: Coding sequence for genetically engineered
      single chain antibody - 9A4 VH - VL.

<400> SEQUENCE: 7
aagctttgga gccttggaga ttttcaacgt gaaaaaatta ttattcgcaa ttcctttagt    60
tgttcctttt tatgcggccc agccggccat ggcccagatc cagttggtgc agtctggtcc   120
tgagctgaag aagcctggag agacagtcaa gatctcctgc aaggcttctg gttataccct   180
cacagactat tcaatacact gggtgaagca ggctccagga aagggtttaa agtggatggg   240
ctggataaac actgagactg gtgagccaac atatgcagat gacttcaagg gacgttttgc   300
cttctctttg gaaacctctg ccagcactgc ctatttgcag atcaacaacc tcaaaaatga   360
ggacacggct acatatttct gtgctagggg cggtagcctt gactactggg gccaaggcac   420
cactctcaca gtctcctcag gtggaggcgg ttcaggcgga ggtggcagcg gcggtggcgg   480
atcgcaaatt gttctcaccc agtctccagt attcatgtct gcatctccag gggagaaggt   540
caccatgacc tgcagtgcca gctcaagtgt aagttacatg tactggtacc agcagaagcc   600
aggatcctcc cccagactcc tgattcatgc acatccaac ctggcttctg gagtccctgt   660
tcgcttcagt ggcggtgggt ctgggacctc ttactctctc acaatcagcc gaatggaggc   720
tgaagatgct gccacttatt actgtcagca gtggagaagt tatacacgga cgttcggtgg   780
aggcaccaag ctggaaatca tagcggccgc acatcatcat caccatcacg ggccgcagaa   840
acaaaaactc atctcagaag aggatctgaa tggggccgca tag                     883

<210> SEQ ID NO 8
<211> LENGTH: 1340
<212> TYPE: DNA
<213> ORGANISM: Artificial Sequence
<220> FEATURE:
<223> OTHER INFORMATION: Description of Artificial Sequence: 9A4 VL -
      VH single chain antibody.
<220> FEATURE:
<221> NAME/KEY: sig_peptide
<222> LOCATION: (293)..(358)

<223> OTHER INFORMATION: pel B signal peptide in pATDFLAG.
<220> FEATURE:
<221> NAME/KEY: mat_peptide
<222> LOCATION: (359)..(1126)
<223> OTHER INFORMATION: Coding sequence for genetically engineered
      single chain antibody - 9A4 VL - VH.

<400> SEQUENCE: 8

```
ctcatgtttg acagcttatc atcgatgaat tccatcactt ccctccgttc atttgtcccc      60
ggtggaaacg aggtcatcat ttccttccga aaaacggtt gcatttaaat cttacatata     120
taatactttc aaagactaca tttgtaagat ttgatgtttg agtcggctga agatcgtac     180 gtaccaatta ttgtttcgtg attgttcaag ccataacact gtagggatag tggaaagagt     240
gcttcatctg gttacgatca atcaaatatt caaacgagg gagacgattt tgatgaaata     300
cctattgcct acggcagccg ctggattgtt attactcgct gcccaaccag ccatggccca     360
aattgttctc acccagtctc cagtattcat gtctgcatct ccaggggaga aggtcaccat     420
gacctgcagt gccagctcaa gtgtaagtta catgtactgg taccagcaga agccaggatc     480
ctcccccaga ctcctgattc atgccacatc caacctggct tctggagtcc ctgttcgctt     540
cagtggcggt gggtctggga cctcttactc tctcacaatc agccgaatgg aggctgaaga     600
tgctgccact tattactgtc agcagtggag aagttataca cggacgttcg gtggaggcac     660
caagctggaa atcatactta gtgcggacga tgcgaaaaag gatgctgcga agaaggatga     720
cgctaagaaa gacgatgcta aaaggacct cgagatccag ttggtgcagt ctggtcctga     780
gctgaagaag cctggagaga cagtcaagat ctcctgcaag gcttctggtt ataccttcac     840
agactattca atacactggg tgaagcaggc tccaggaaag ggtttaaagt ggatgggctg     900
gataaacact gagactggtg agccaacata tgcagatgac ttcaagggac ggtttgcctt     960
ctctttggaa acctctgcca gcactgccta tttgcagatc aacaacctca aaatgaggga    1020
cacggctaca tatttctgtg ctaggggcgg tagccttgac tactggggcc aaggcaccac    1080
tctcacagtc tcctcagcta gcgactacaa ggacgatgat gacaaataaa aacctagcga    1140
tgaatccgtc aaaacatcat cttacataaa gtcacttggt gatcaagctc atatcattgt    1200
ccggcaatgg tgtgggcttt ttttgttttc tatctttaaa gatcatgtga agaaaaacgg    1260
gaaaatcggt ctgcgggaaa ggaccgggtt tttgtcgaaa tcataggcga atgggttgga    1320
ttgtgacaaa attcggatcc                                                1340
```

<210> SEQ ID NO 9
<211> LENGTH: 907
<212> TYPE: DNA
<213> ORGANISM: Artificial Sequence
<220> FEATURE:
<223> OTHER INFORMATION: Description of Artificial Sequence: 5109
      VH - VL single chain antibody.
<220> FEATURE:
<221> NAME/KEY: sig_peptide
<222> LOCATION: (29)..(94)
<223> OTHER INFORMATION: Engineered signal peptide in pCANTAB6;
      initiator methionine is coded for most likely by gtg codon.
<220> FEATURE:
<221> NAME/KEY: mat_peptide
<222> LOCATION: (95)..(895)
<223> OTHER INFORMATION: Coding sequence for genetically engineered
      single chain antibody - 5109 VH - VL.

<400> SEQUENCE: 9

```
aagctttgga gccttggaga ttttcaacgt gaaaaaatta ttattcgcaa ttcctttagt      60
tgttcctttt tatgcggccc agccggccat ggccgaagtg cagctggtgg agtctggggg     120
```

```
aggctcagtg cagcctggag ggtccctgaa actctcctgt gcagcctctg gattcacttt    180
caatacctac ggcatgtctt gggttcgcca gactccagac aagaggctgg agtgggtcgc    240
aaccattaat agtaatggtg gtctcacctt ttatgcagac agtgtgaagg gccgattcac    300
catttccaga gacaatgcca aaaacaccct gtatctgcaa atgaacaggc tgaagtctgg    360
ggactcaggc atgtattact gtgtaagagg atatagtaat tacgctcgct ggggccaagg    420
ggcgctggtc actgtctcga gtggtggagg cggttcaggc ggaggtggca gcggcggtgg    480
cggatcgtct gatgttgtga tgacccaaac tccactcact ttgtcggtta ccattggaca    540
atcagcctcc atctcttgca agtcaagtca gagcctctta ggtagtgatg gattgacata    600
tttgatttgg ttgttgcaga ggccaggcca gtctccaaag cgcctaatct ttctggtgtc    660
tgaattggac tctggagtcc ctgacaggtt cactggcagt ggatcaggga cagatttcac    720
actgaaaatc agcagagcgg aggctgaaga tttgggagtt tattattgct gccaaggtac    780
acattttcct cacacgttcg gtgctgggac caagctggag ctgaaagcgg ccgcagaact    840
aaaactcatc tcagaagagg atctgaatgg ggccgcacat caccaccatc accattaata    900
agaattc                                                              907

<210> SEQ ID NO 10
<211> LENGTH: 348
<212> TYPE: DNA
<213> ORGANISM: Mus musculus
<220> FEATURE:
<221> NAME/KEY: V_region
<222> LOCATION: (1)..(348)
<223> OTHER INFORMATION: Mature 5109 VH region.

<400> SEQUENCE: 10
gaagtgcagc tggtggagtc tgggggaggc tcagtgcagc ctggagggtc cctgaaactc     60
tcctgtgcag cctctggatt cactttcaat acctacggca tgtcttgggt tcgccagact    120
ccagacaaga ggctggagtg gtcgcaacc attaatagta atggtggtct cacctttat    180 gcagacagtg tgaagggccg attcaccatt tccagagaca atgccaaaaa caccctgtat    240
ctgcaaatga acaggctgaa gtctggggac tcaggcatgt attactgtgt aagaggatat    300
agtaattacg ctcgctgggg ccaaggggcg ctggtcactg tctctgca                 348

<210> SEQ ID NO 11
<211> LENGTH: 336
<212> TYPE: DNA
<213> ORGANISM: Mus musculus
<220> FEATURE:
<221> NAME/KEY: V_region
<222> LOCATION: (1)..(336)
<223> OTHER INFORMATION: Mature 5109 VL region.

<400> SEQUENCE: 11
gatgttgtga tgacccaaac tccactcact ttgtcggtta ccattggaca atcagcctcc     60
atctcttgca agtcaagtca gagcctctta ggtagtgatg gattgacata tttgatttgg    120
ttgttgcaga ggccaggcca gtctccaaag cgcctaatct ttctggtgtc tgaattggac    180
tctggagtcc ctgacaggtt cactggcagt ggatcaggga cagatttcac actgaaaatc    240
agcagagtgg aggctgaaga tttgggagtt tattattgct gccaaggtac acattttcct    300
cacacgttcg gtgctgggac caagctggag ctgaaa                               336

<210> SEQ ID NO 12
```

```
<211> LENGTH: 13
<212> TYPE: PRT
<213> ORGANISM: Homo sapiens
<220> FEATURE:
<221> NAME/KEY: MOD_RES
<222> LOCATION: (2)
<223> OTHER INFORMATION: Type II collagen fragment with 4Hyp.
<220> FEATURE:
<221> NAME/KEY: MOD_RES
<222> LOCATION: (8)
<223> OTHER INFORMATION: Type II collagen fragment with 4Hyp.
<220> FEATURE:
<221> NAME/KEY: MOD_RES
<222> LOCATION: (11)
<223> OTHER INFORMATION: Type II collagen fragment with 4Hyp.

<400> SEQUENCE: 12

Ala Xaa Gly Glu Asp Gly Arg Xaa Gly Pro Xaa Gly Pro
 1               5                  10

<210> SEQ ID NO 13
<211> LENGTH: 20
<212> TYPE: PRT
<213> ORGANISM: Homo sapiens
<220> FEATURE:
<221> NAME/KEY: MOD_RES
<222> LOCATION: (9)
<223> OTHER INFORMATION: Type II collagen fragment with 4Hyp.
<220> FEATURE:
<221> NAME/KEY: MOD_RES
<222> LOCATION: (15)
<223> OTHER INFORMATION: Type II collagen fragment with 4Hyp.
<220> FEATURE:
<221> NAME/KEY: MOD_RES
<222> LOCATION: (18)
<223> OTHER INFORMATION: Type II collagen fragment with 4Hyp.

<400> SEQUENCE: 13

Gly Lys Val Gly Pro Ser Gly Ala Xaa Gly Glu Asp Gly Arg Xaa Gly
 1               5                  10                  15

Pro Xaa Gly Pro
            20

<210> SEQ ID NO 14
<211> LENGTH: 9
<212> TYPE: PRT
<213> ORGANISM: Homo sapiens
<220> FEATURE:
<221> NAME/KEY: DOMAIN
<222> LOCATION: (1)..(9)
<223> OTHER INFORMATION: Type II collagen fragment.

<400> SEQUENCE: 14

Ala Glu Gly Pro Pro Gly Pro Gln Gly
 1               5

<210> SEQ ID NO 15
<211> LENGTH: 10
<212> TYPE: PRT
<213> ORGANISM: Homo sapiens
<220> FEATURE:
<221> NAME/KEY: MOD_RES
<222> LOCATION: (3)
<223> OTHER INFORMATION: Type II collagen fragment with 4Hyp.
<220> FEATURE:
<221> NAME/KEY: SITE
<222> LOCATION: (7)
<223> OTHER INFORMATION: Collagenase cleaves on the - COOH side of
                        residue 7.

<400> SEQUENCE: 15
```

```
Gly Pro Xaa Gly Pro Gln Gly Leu Ala Gly
 1               5                  10
```

<210> SEQ ID NO 16
<211> LENGTH: 7
<212> TYPE: PRT
<213> ORGANISM: Homo sapiens
<220> FEATURE:
<221> NAME/KEY: DOMAIN
<222> LOCATION: (1)..(7)
<223> OTHER INFORMATION: Type I collagen fragment.

<400> SEQUENCE: 16

```
Gly Thr Pro Gly Pro Gln Gly
 1               5
```

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence:  Modified
                        Type II collagen fragment.

<400> SEQUENCE: 17

```
Cys Ala Glu Gly Pro Pro Gly Pro Gln Gly
 1               5                  10
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Modified
      Type II collagen fragment.

<400> SEQUENCE: 18

```
Cys Gly Glu Pro Gly Asp Asp Gly Pro Ser
 1               5                  10
```

<210> SEQ ID NO 19
<211> LENGTH: 9
<212> TYPE: PRT
<213> ORGANISM: Homo sapiens
<220> FEATURE:
<221> NAME/KEY: DOMAIN
<222> LOCATION: (1)..(9)
<223> OTHER INFORMATION: Type II collagen fragment.

<400> SEQUENCE: 19

```
Gly Glu Pro Gly Asp Asp Gly Pro Ser
 1               5
```

<210> SEQ ID NO 20
<211> LENGTH: 19
<212> TYPE: PRT
<213> ORGANISM: Homo sapiens
<220> FEATURE:
<221> NAME/KEY: DOMAIN
<222> LOCATION: (1)..(19)
<223> OTHER INFORMATION: Type II collagen fragment.

<400> SEQUENCE: 20

```
Gly Glu Pro Gly Asp Asp Gly Pro Ser Gly Ala Glu Gly Pro Pro Gly
 1               5                  10                  15
Pro Gln Gly
```

-continued

```
<210> SEQ ID NO 21
<211> LENGTH: 20
<212> TYPE: DNA
<213> ORGANISM: Mus musculus

<400> SEQUENCE: 21
ggtgaagttg atgtcttgtg                                           20

<210> SEQ ID NO 22
<211> LENGTH: 23
<212> TYPE: DNA
<213> ORGANISM: Mus musculus

<400> SEQUENCE: 22
gaccttgcat ttgaactcct tgc                                       23

<210> SEQ ID NO 23
<211> LENGTH: 20
<212> TYPE: DNA
<213> ORGANISM: Mus musculus

<400> SEQUENCE: 23
ggctgtggaa cttgctattc                                           20

<210> SEQ ID NO 24
<211> LENGTH: 20
<212> TYPE: DNA
<213> ORGANISM: Mus musculus

<400> SEQUENCE: 24
gggtgtggac cttgccattc                                           20

<210> SEQ ID NO 25
<211> LENGTH: 20
<212> TYPE: DNA
<213> ORGANISM: Mus musculus

<400> SEQUENCE: 25
gggtgtggac cttgctattc                                           20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:  Mixed
      oligonucleotide set as PCR primers for murine VH
      signal peptide region.

<400> SEQUENCE: 26
ggstgtggam cttgcyattc                                           20

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:  Mixed
      oligonucleotide set as PCR primers for murine VL
      signal peptide region.

<400> SEQUENCE: 27
gcttcctgct aatcaktg                                             18

<210> SEQ ID NO 28
```

```
<211> LENGTH: 21
<212> TYPE: DNA
<213> ORGANISM: Mus musculus

<400> SEQUENCE: 28
ggcagcagat ccagggggcca g                                          21

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence:  Murine
      light chain Kappa region primer with Hind III site.

<400> SEQUENCE: 29
gggaaagctt gttaactgct cactggatgg tgg                              33

<210> SEQ ID NO 30
<211> LENGTH: 22
<212> TYPE: DNA
<213> ORGANISM: Erwinia carotovora

<400> SEQUENCE: 30
ctattgccta cggcagccgc tg                                          22

<210> SEQ ID NO 31
<211> LENGTH: 20
<212> TYPE: DNA
<213> ORGANISM: Bacillus licheniformif 749/C

<400> SEQUENCE: 31
cacatgatct ttaaagatag                                             20

<210> SEQ ID NO 32
<211> LENGTH: 136
<212> TYPE: PRT
<213> ORGANISM: Mus musculus
<220> FEATURE:
<221> NAME/KEY: SIGNAL
<222> LOCATION: (1)..(11)
<223> OTHER INFORMATION: Portion of 9A4 VH signal peptide.
<220> FEATURE:
<221> NAME/KEY: DOMAIN
<222> LOCATION: (12)..(126)
<223> OTHER INFORMATION: Mature 9A4 VH.
<220> FEATURE:
<221> NAME/KEY: DOMAIN
<222> LOCATION: (127)..(136)
<223> OTHER INFORMATION: Portion of murine IgGl CH1 constant domain.

<400> SEQUENCE: 32

Phe Leu Met Ala Ala Ala Gln Ser Ile Gln Ala Gln Ile Gln Leu Val
 1               5                  10                  15

Gln Ser Gly Pro Glu Leu Lys Lys Pro Gly Glu Thr Val Lys Ile Ser
                20                  25                  30

Cys Lys Ala Ser Gly Tyr Thr Phe Thr Asp Tyr Ser Ile His Trp Val
            35                  40                  45

Lys Gln Ala Pro Gly Lys Gly Leu Lys Trp Met Gly Trp Ile Asn Thr
        50                  55                  60

Glu Thr Gly Glu Pro Thr Tyr Ala Asp Asp Phe Lys Gly Arg Phe Ala
 65                 70                  75                  80

Phe Ser Leu Glu Thr Ser Ala Ser Thr Ala Tyr Leu Gln Ile Asn Asn
                85                  90                  95
```

```
Leu Lys Asn Glu Asp Thr Ala Thr Tyr Phe Cys Ala Arg Gly Gly Ser
            100                 105                 110

Leu Asp Tyr Trp Gly Gln Gly Thr Thr Leu Thr Val Ser Ser Ala Lys
        115                 120                 125

Thr Thr Pro Pro Ser Val Tyr Pro
    130                 135

<210> SEQ ID NO 33
<211> LENGTH: 119
<212> TYPE: PRT
<213> ORGANISM: Mus musculus
<220> FEATURE:
<221> NAME/KEY: SIGNAL
<222> LOCATION: (1)..(7)
<223> OTHER INFORMATION: Portion of 9A4 VL signal peptide.
<220> FEATURE:
<221> NAME/KEY: DOMAIN
<222> LOCATION: (8)..(113)
<223> OTHER INFORMATION: Mature 9A4 VL.
<220> FEATURE:
<221> NAME/KEY: DOMAIN
<222> LOCATION: (114)..(119)
<223> OTHER INFORMATION: Portion of murine C kappa constant domain.

<400> SEQUENCE: 33

Ser Val Ile Leu Ser Arg Gly Gln Ile Val Leu Thr Gln Ser Pro Val
  1               5                  10                  15

Phe Met Ser Ala Ser Pro Gly Glu Lys Val Thr Met Thr Cys Ser Ala
             20                  25                  30

Ser Ser Ser Val Ser Tyr Met Tyr Trp Tyr Gln Gln Lys Pro Gly Ser
         35                  40                  45

Ser Pro Arg Leu Leu Ile His Ala Thr Ser Asn Leu Ala Ser Gly Val
     50                  55                  60

Pro Val Arg Phe Ser Gly Gly Ser Gly Thr Ser Tyr Ser Leu Thr
 65                  70                  75                  80

Ile Ser Arg Met Glu Ala Glu Asp Ala Ala Thr Tyr Tyr Cys Gln Gln
                 85                  90                  95

Trp Arg Ser Tyr Thr Arg Thr Phe Gly Gly Gly Thr Lys Leu Glu Ile
            100                 105                 110

Ile Arg Ala Asp Ala Ala Pro
        115

<210> SEQ ID NO 34
<211> LENGTH: 47
<212> TYPE: DNA
<213> ORGANISM: Artificial Sequence
<220> FEATURE:
<223> OTHER INFORMATION: Description of Artificial Sequence:   PCR - SOE
      primer for 5' 9A4 VH region, including an Sfi I
      restriction endonuclease site.

<400> SEQUENCE: 34
gaggaggccc agccggccat ggcccagatc cagttggtgc agtctgg                    47

<210> SEQ ID NO 35
<211> LENGTH: 61
<212> TYPE: DNA
<213> ORGANISM: Artificial Sequence
<220> FEATURE:
<223> OTHER INFORMATION: Description of Artificial Sequence:   PCR - SOE
      primer for 3' 9A4 VH region, including linker
      segment of scFv for assembly PCR reaction with 9A4
      VL.

<400> SEQUENCE: 35
```

```
gccgctgcca cctccgcctg aaccgcctcc accactcgag actgtgagag tggtgccttg        60
g                                                                        61
```

<210> SEQ ID NO 36
<211> LENGTH: 56
<212> TYPE: DNA
<213> ORGANISM: Artificial Sequence
<220> FEATURE:
<223> OTHER INFORMATION: Description of Artificial Sequence:   PCR - SOE
      primer 5' 9A4 VL region, including overlap into
      scFv linker segment.

<400> SEQUENCE: 36

```
ggttcaggcg gaggtggcag cggcggtggc ggatcgcaaa ttgttctcac ccagtc            56
```

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence:   PCR - SOE
      primer for 3' 9A4 VL region, including a Not I
      restriction endonuclease site.

<400> SEQUENCE: 37

```
gaaggacgcc ggcgtatgat ttccagcttg gtgcctcc                                38
```

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence:   9A4 scFv
      PCR primer, including a Not I restriction endonuclease
      site.

<400> SEQUENCE: 38

```
aagaagcggc cgctatgatt tccagcttgg tgcctc                                  36
```

<210> SEQ ID NO 39
<211> LENGTH: 23
<212> TYPE: DNA
<213> ORGANISM: Escherichia coli

<400> SEQUENCE: 39

```
agcggataac aatttcacac agg                                                23
```

<210> SEQ ID NO 40
<211> LENGTH: 284
<212> TYPE: PRT
<213> ORGANISM: Artificial Sequence
<220> FEATURE:
<223> OTHER INFORMATION: Description of Artificial Sequence:9A4 scFv VH
      -VL.
<220> FEATURE:
<221> NAME/KEY: SIGNAL
<222> LOCATION: (1)..(22)
<223> OTHER INFORMATION: pCANTAB6 signal peptide; Val at position 1 is
      most likely the initiator Met.
<220> FEATURE:
<221> NAME/KEY: DOMAIN
<222> LOCATION: (23)..(137)
<223> OTHER INFORMATION: 9A4 VH domain.
<220> FEATURE:
<221> NAME/KEY: DOMAIN
<222> LOCATION: (138)..(152)
<223> OTHER INFORMATION: 15 amino acid linker.
<220> FEATURE:

```
<221> NAME/KEY: DOMAIN
<222> LOCATION: (153)..(258)
<223> OTHER INFORMATION: 9A4 VL domain.
<220> FEATURE:
<221> NAME/KEY: SITE
<222> LOCATION: (262)..(267)
<223> OTHER INFORMATION: His tag.
<220> FEATURE:
<221> NAME/KEY: SITE
<222> LOCATION: (271)..(280)
<223> OTHER INFORMATION: myc tag.

<400> SEQUENCE: 40

Met Lys Lys Leu Leu Phe Ala Ile Pro Leu Val Val Pro Phe Tyr Ala
 1               5                  10                  15

Ala Gln Pro Ala Met Ala Gln Ile Gln Leu Val Gln Ser Gly Pro Glu
             20                  25                  30

Leu Lys Lys Pro Gly Glu Thr Val Lys Ile Ser Cys Lys Ala Ser Gly
         35                  40                  45

Tyr Thr Phe Thr Asp Tyr Ser Ile His Trp Val Lys Gln Ala Pro Gly
     50                  55                  60

Lys Gly Leu Lys Trp Met Gly Trp Ile Asn Thr Glu Thr Gly Glu Pro
 65                  70                  75                  80

Thr Tyr Ala Asp Asp Phe Lys Gly Arg Phe Ala Phe Ser Leu Glu Thr
                 85                  90                  95

Ser Ala Ser Thr Ala Tyr Leu Gln Ile Asn Asn Leu Lys Asn Glu Asp
            100                 105                 110

Thr Ala Thr Tyr Phe Cys Ala Arg Gly Gly Ser Leu Asp Tyr Trp Gly
        115                 120                 125

Gln Gly Thr Thr Leu Thr Val Ser Ser Gly Gly Gly Ser Gly Gly
    130                 135                 140

Gly Gly Ser Gly Gly Gly Ser Gln Ile Val Leu Thr Gln Ser Pro
145                 150                 155                 160

Val Phe Met Ser Ala Ser Pro Gly Glu Lys Val Thr Met Thr Cys Ser
                165                 170                 175

Ala Ser Ser Ser Val Ser Tyr Met Tyr Trp Tyr Gln Gln Lys Pro Gly
            180                 185                 190

Ser Ser Pro Arg Leu Leu Ile His Ala Thr Ser Asn Leu Ala Ser Gly
        195                 200                 205

Val Pro Val Arg Phe Ser Gly Gly Ser Gly Thr Ser Tyr Ser Leu
    210                 215                 220

Thr Ile Ser Arg Met Glu Ala Glu Asp Ala Ala Thr Tyr Tyr Cys Gln
225                 230                 235                 240

Gln Trp Arg Ser Tyr Thr Arg Thr Phe Gly Gly Thr Lys Leu Glu
                245                 250                 255

Ile Ile Ala Ala Ala His His His His His His Gly Ala Ala Glu Gln
            260                 265                 270

Lys Leu Ile Ser Glu Glu Asp Leu Asn Gly Ala Ala
        275                 280

<210> SEQ ID NO 41
<211> LENGTH: 21
<212> TYPE: DNA
<213> ORGANISM: Bacteriophage fd

<400> SEQUENCE: 41
gtcgtctttc cagacgttag t                                           21
```

```
<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence:  Single
      chain antibody linker sequence.

<400> SEQUENCE: 42

Leu Ser Ala Asp Asp Ala Lys Lys Asp Ala Ala Lys Lys Asp Asp Ala
 1               5                  10                  15

Lys Lys Asp Asp Ala Lys Lys Asp Leu
            20                  25

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence:PCR - SOE
      primer for 5' 9A4 VL region, including an Nco I
      restriction endonuclease site.

<400> SEQUENCE: 43
gaggagccat ggcccaaatt gttctcaccc agtc                                34

<210> SEQ ID NO 44
<211> LENGTH: 79
<212> TYPE: DNA
<213> ORGANISM: Artificial Sequence
<220> FEATURE:
<223> OTHER INFORMATION: Description of Artificial Sequence:  PCR - SOE
      primer for 3' 9A4 VL region, including linker
      segment of scFv for assembly PCR reaction with 9A4
      VH.

<400> SEQUENCE: 44
ctttcttagc gtcatccttc ttcgcagcat ccttttttcgc atcgtccgca ctaagcttga    60
tttccagctt ggtgcctcc                                                 79

<210> SEQ ID NO 45
<211> LENGTH: 70
<212> TYPE: DNA
<213> ORGANISM: Artificial Sequence
<220> FEATURE:
<223> OTHER INFORMATION: Description of Artificial Sequence:  PCR - SOE
      primer for 5' 9A4 VH region, including linker
      segment of scFv for assembly PCR reaction with 9A4
      VL.

<400> SEQUENCE: 45
ctgcgaagaa ggatgacgct aagaaagacg atgctaaaaa ggacctcgag atccagttgg    60
tgcagtctgg                                                           70

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence:  PCR - SOE
      primer for 3' 9A4 VH region, including an Nhe I
      restriction endonuclease site.

<400> SEQUENCE: 46
gaggaagcta gctgaggaga ctgtgagagt ggtgcc                              36
```

```
<210> SEQ ID NO 47
<211> LENGTH: 278
<212> TYPE: PRT
<213> ORGANISM: Artificial Sequence
<220> FEATURE:
<223> OTHER INFORMATION: Description of Artificial Sequence:  9A4 scFv
      VL - VH.
<220> FEATURE:
<221> NAME/KEY: SIGNAL
<222> LOCATION: (1)..(22)
<223> OTHER INFORMATION: pel B signal peptide in pATDFLAG.
<220> FEATURE:
<221> NAME/KEY: DOMAIN
<222> LOCATION: (23)..(128)
<223> OTHER INFORMATION: 9A4 VL domain.
<220> FEATURE:
<221> NAME/KEY: DOMAIN
<222> LOCATION: (129)..(153)
<223> OTHER INFORMATION: 25 amino acid linker.
<220> FEATURE:
<221> NAME/KEY: DOMAIN
<222> LOCATION: (154)..(268)
<223> OTHER INFORMATION: 9A4 VH domain.
<220> FEATURE:
<221> NAME/KEY: SITE
<222> LOCATION: (271)..(278)
<223> OTHER INFORMATION: FLAG tag.

<400> SEQUENCE: 47

Met Lys Tyr Leu Leu Pro Thr Ala Ala Ala Gly Leu Leu Leu Leu Ala
  1               5                  10                  15

Ala Gln Pro Ala Met Ala Gln Ile Val Leu Thr Gln Ser Pro Val Phe
                 20                  25                  30

Met Ser Ala Ser Pro Gly Glu Lys Val Thr Met Thr Cys Ser Ala Ser
             35                  40                  45

Ser Ser Val Ser Tyr Met Tyr Trp Tyr Gln Gln Lys Pro Gly Ser Ser
         50                  55                  60

Pro Arg Leu Leu Ile His Ala Thr Ser Asn Leu Ala Ser Gly Val Pro
 65                  70                  75                  80

Val Arg Phe Ser Gly Gly Gly Ser Gly Thr Ser Tyr Ser Leu Thr Ile
                 85                  90                  95

Ser Arg Met Glu Ala Glu Asp Ala Ala Thr Tyr Tyr Cys Gln Gln Trp
            100                 105                 110

Arg Ser Tyr Thr Arg Thr Phe Gly Gly Gly Thr Lys Leu Glu Ile Ile
        115                 120                 125

Leu Ser Ala Asp Asp Ala Lys Lys Asp Ala Ala Lys Lys Asp Asp Ala
130                 135                 140

Lys Lys Asp Asp Ala Lys Lys Asp Leu Glu Ile Gln Leu Val Gln Ser
145                 150                 155                 160

Gly Pro Glu Leu Lys Lys Pro Gly Glu Thr Val Lys Ile Ser Cys Lys
                165                 170                 175

Ala Ser Gly Tyr Thr Phe Thr Asp Tyr Ser Ile His Trp Val Lys Gln
            180                 185                 190

Ala Pro Gly Lys Gly Leu Lys Trp Met Gly Trp Ile Asn Thr Glu Thr
        195                 200                 205

Gly Glu Pro Thr Tyr Ala Asp Asp Phe Lys Gly Arg Phe Ala Phe Ser
    210                 215                 220

Leu Glu Thr Ser Ala Ser Thr Ala Tyr Leu Gln Ile Asn Asn Leu Lys
225                 230                 235                 240

Asn Glu Asp Thr Ala Thr Tyr Phe Cys Ala Arg Gly Gly Ser Leu Asp
                245                 250                 255

Tyr Trp Gly Gln Gly Thr Thr Leu Thr Val Ser Ser Ala Ser Asp Tyr
```

```
                        260                 265                 270
Lys Asp Asp Asp Lys
        275

<210> SEQ ID NO 48
<211> LENGTH: 116
<212> TYPE: PRT
<213> ORGANISM: Mus musculus
<220> FEATURE:
<221> NAME/KEY: DOMAIN
<222> LOCATION: (1)..(116)
<223> OTHER INFORMATION: Mature 5109 VH.

<400> SEQUENCE: 48

Glu Val Gln Leu Val Glu Ser Gly Gly Gly Ser Val Gln Pro Gly Gly
  1               5                  10                  15

Ser Leu Lys Leu Ser Cys Ala Ala Ser Gly Phe Thr Phe Asn Thr Tyr
             20                  25                  30

Gly Met Ser Trp Val Arg Gln Thr Pro Asp Lys Arg Leu Glu Trp Val
         35                  40                  45

Ala Thr Ile Asn Ser Asn Gly Gly Leu Thr Phe Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Arg Leu Lys Ser Gly Asp Ser Gly Met Tyr Tyr Cys
                 85                  90                  95

Val Arg Gly Tyr Ser Asn Tyr Ala Arg Trp Gly Gln Gly Ala Leu Val
            100                 105                 110

Thr Val Ser Ala
        115

<210> SEQ ID NO 49
<211> LENGTH: 112
<212> TYPE: PRT
<213> ORGANISM: Mus musculus
<220> FEATURE:
<221> NAME/KEY: DOMAIN
<222> LOCATION: (1)..(112)
<223> OTHER INFORMATION: Mature 5109 VL.

<400> SEQUENCE: 49

Asp Val Val Met Thr Gln Thr Pro Leu Thr Leu Ser Val Thr Ile Gly
  1               5                  10                  15

Gln Ser Ala Ser Ile Ser Cys Lys Ser Ser Gln Ser Leu Leu Gly Ser
             20                  25                  30

Asp Gly Leu Thr Tyr Leu Ile Trp Leu Leu Gln Arg Pro Gly Gln Ser
         35                  40                  45

Pro Lys Arg Leu Ile Phe Leu Val Ser Glu Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Cys Gln Gly
                 85                  90                  95

Thr His Phe Pro His Thr Phe Gly Ala Gly Thr Lys Leu Glu Leu Lys
            100                 105                 110

<210> SEQ ID NO 50
<211> LENGTH: 24
<212> TYPE: DNA
<213> ORGANISM: Mus musculus
```

<400> SEQUENCE: 50
gaagtgcagc tggtggagtc tggg                                           24

<210> SEQ ID NO 51
<211> LENGTH: 20
<212> TYPE: DNA
<213> ORGANISM: Mus musculus

<400> SEQUENCE: 51
gatgttgtga tgacccaaac                                                20

<210> SEQ ID NO 52
<211> LENGTH: 24
<212> TYPE: DNA
<213> ORGANISM: Mus musculus

<400> SEQUENCE: 52
ctgatcagtc caactgttca ggac                                           24

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence:  Sequencing
      oligonucleotide.

<400> SEQUENCE: 53
gtaaaacgac ggccag                                                    16

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence:  Sequencing
      oligonucleotide.

<400> SEQUENCE: 54
caggaaacag ctatgac                                                   17

<210> SEQ ID NO 55
<211> LENGTH: 49
<212> TYPE: DNA
<213> ORGANISM: Artificial Sequence
<220> FEATURE:
<223> OTHER INFORMATION: Description of Artificial Sequence:  PCR - SOE
      primer for 5' 5109 VH region, including an Sfi I
      restriction endonuclease site.

<400> SEQUENCE: 55
gaagagcggc ccagccggcc atggccgaag tgcagctggt ggagtctgg                49

<210> SEQ ID NO 56
<211> LENGTH: 74
<212> TYPE: DNA
<213> ORGANISM: Artificial Sequence
<220> FEATURE:
<223> OTHER INFORMATION: Description of Artificial Sequence:  PCR - SOE
      primer for 3' 5109 VH region including linker
      segment of scFv for assembly PCR reaction with
      5109 VL.

<400> SEQUENCE: 56
cgatccgcca ccgccgctgc cacctccgcc tgaaccgcct ccaccactcg agacagtgac    60

```
cagcgcccct tggc                                                    74

<210> SEQ ID NO 57
<211> LENGTH: 66
<212> TYPE: DNA
<213> ORGANISM: Artificial Sequence
<220> FEATURE:
<223> OTHER INFORMATION: Description of Artificial Sequence:  PCR - SOE
      primer for 5' 5109 VL region, including overlap
      into scFv linker segment.

<400> SEQUENCE: 57
ggttcaggcg gaggtggcag cggcggtggc ggatcgtctg atgttgtgat gacccaaact    60
ccactc                                                              66

<210> SEQ ID NO 58
<211> LENGTH: 87
<212> TYPE: DNA
<213> ORGANISM: Artificial Sequence
<220> FEATURE:
<223> OTHER INFORMATION: Description of Artificial Sequence:  PCR - SOE
      primer for 3' 5109 VL region, Ser version,
      including a Not I restriction endonuclease site.

<400> SEQUENCE: 58
ggaaggagcg gccgctttca gctccagctt ggtcccagca ccgaacgtgt gaggaaaatg    60
tgtaccttgg gagcaataat aaactcc                                       87

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence:  PCR - SOE
      primer for 3' 5109 VL region, Cys version,
      including a Not I restriction endonuclease site.

<400> SEQUENCE: 59
ggaaggagcg gccgctttca gctccagctt ggtagc                             36

<210> SEQ ID NO 60
<211> LENGTH: 21
<212> TYPE: DNA
<213> ORGANISM: Homo sapiens

<400> SEQUENCE: 60
ctcttctgag atgagttttt g                                             21

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:  Sequencing
      oligonucleotide.  Primes in Gly4Ser linker region.

<400> SEQUENCE: 61
gaggcggttc aggcggag                                                 18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence:  Sequencing
```

-continued oligonucleotide. Primes in Gly4Ser linker region.

<400> SEQUENCE: 62
gatccgccac cgccgctg                                                  18

<210> SEQ ID NO 63
<211> LENGTH: 289
<212> TYPE: PRT
<213> ORGANISM: Artificial Sequence
<220> FEATURE:
<223> OTHER INFORMATION: Description of Artificial Sequence:  5109 VH -
      VL scFv.
<220> FEATURE:
<221> NAME/KEY: SIGNAL
<222> LOCATION: (1)..(22)
<223> OTHER INFORMATION: pCANTAB6 signal peptide; Val at position 1 is
      most likely initiator Met.
<220> FEATURE:
<221> NAME/KEY: DOMAIN
<222> LOCATION: (23)..(138)
<223> OTHER INFORMATION: 5109 VH domain.
<220> FEATURE:
<221> NAME/KEY: DOMAIN
<222> LOCATION: (139)..(154)
<223> OTHER INFORMATION: 16 amino acid linker.
<220> FEATURE:
<221> NAME/KEY: DOMAIN
<222> LOCATION: (155)..(266)
<223> OTHER INFORMATION: 5109 VL domain.
<220> FEATURE:
<221> NAME/KEY: SITE
<222> LOCATION: (270)..(279)
<223> OTHER INFORMATION: myc tag.
<220> FEATURE:
<221> NAME/KEY: SITE
<222> LOCATION: (284)..(289)
<223> OTHER INFORMATION: His tag.

<400> SEQUENCE: 63

Met Lys Lys Leu Leu Phe Ala Ile Pro Leu Val Val Pro Phe Tyr Ala
 1               5                  10                  15

Ala Gln Pro Ala Met Ala Glu Val Gln Leu Val Glu Ser Gly Gly Gly
                20                  25                  30

Ser Val Gln Pro Gly Gly Ser Leu Lys Leu Ser Cys Ala Ala Ser Gly
        35                  40                  45

Phe Thr Phe Asn Thr Tyr Gly Met Ser Trp Val Arg Gln Thr Pro Asp
    50                  55                  60

Lys Arg Leu Glu Trp Val Ala Thr Ile Asn Ser Asn Gly Gly Leu Thr
65                  70                  75                  80

Phe Tyr Ala Asp Ser Val Lys Gly Arg Phe Thr Ile Ser Arg Asp Asn
                85                  90                  95

Ala Lys Asn Thr Leu Tyr Leu Gln Met Asn Arg Leu Lys Ser Gly Asp
            100                 105                 110

Ser Gly Met Tyr Tyr Cys Val Arg Gly Tyr Ser Asn Tyr Ala Arg Trp
        115                 120                 125

Gly Gln Gly Ala Leu Val Thr Val Ser Ser Gly Gly Gly Gly Ser Gly
    130                 135                 140

Gly Gly Ser Gly Gly Gly Ser Ser Asp Val Val Met Thr Gln
145                 150                 155                 160

Thr Pro Leu Thr Leu Ser Val Thr Ile Gly Gln Ser Ala Ser Ile Ser
                165                 170                 175

Cys Lys Ser Ser Gln Ser Leu Leu Gly Ser Asp Gly Leu Thr Tyr Leu
            180                 185                 190

Ile Trp Leu Leu Gln Arg Pro Gly Gln Ser Pro Lys Arg Leu Ile Phe

```
                 195                 200                 205
Leu Val Ser Glu Leu Asp Ser Gly Val Pro Asp Arg Phe Thr Gly Ser
        210                 215                 220

Gly Ser Gly Thr Asp Phe Thr Leu Lys Ile Ser Arg Ala Glu Ala Glu
225                 230                 235                 240

Asp Leu Gly Val Tyr Tyr Cys Cys Gln Gly Thr His Phe Pro His Thr
                245                 250                 255

Phe Gly Ala Gly Thr Lys Leu Glu Leu Lys Ala Ala Ala Glu Gln Lys
            260                 265                 270

Leu Ile Ser Glu Glu Asp Leu Asn Ala Ala Ala His His His His His
        275                 280                 285

His

<210> SEQ ID NO 64
<211> LENGTH: 21
<212> TYPE: PRT
<213> ORGANISM: Homo sapiens
<220> FEATURE:
<221> NAME/KEY: MOD_RES
<222> LOCATION: (17)
<223> OTHER INFORMATION: Type II human collagen fragment with 4Hyp.

<400> SEQUENCE: 64

Glu Lys Gly Glu Pro Gly Asp Asp Ala Pro Ser Gly Ala Glu Gly Pro
1               5                   10                  15

Xaa Gly Pro Gln Gly
            20

<210> SEQ ID NO 65
<211> LENGTH: 62
<212> TYPE: DNA
<213> ORGANISM: Artificial Sequence
<220> FEATURE:
<223> OTHER INFORMATION: Description of Artificial Sequence:  PCR
      spiking oligonucleotide.
<220> FEATURE:
<221> NAME/KEY: misc_difference
<222> LOCATION: (25)..(51)
<223> OTHER INFORMATION: 9A4 scFv PCR spiking oligonucleotide.  Level of
      spiking = 10% with nucleotides other than shown in
      this segment.  Sequence shown represents original.

<400> SEQUENCE: 65
gactgtgaga gtggtgcctt ggccccagta gtcaaggcta ccgcccctag cacagaaata      60
tg                                                                    62

<210> SEQ ID NO 66
<211> LENGTH: 26
<212> TYPE: DNA
<213> ORGANISM: Mus musculus
<220> FEATURE:
<221> NAME/KEY: V_region
<222> LOCATION: (1)..(26)
<223> OTHER INFORMATION: Portion of the JH segment of the 9A4 VH used as
      a PCR primer.

<400> SEQUENCE: 66
gccaaggcac cactctcaca gtctcc                                          26

<210> SEQ ID NO 67
<211> LENGTH: 21
<212> TYPE: PRT
<213> ORGANISM: Homo sapiens
<220> FEATURE:
```

-continued

```
<221> NAME/KEY: MOD_RES
<222> LOCATION: (3)
<223> OTHER INFORMATION: Type II Collagen Fragment with 4Hyp.
<220> FEATURE:
<221> NAME/KEY: MOD_RES
<222> LOCATION: (6)
<223> OTHER INFORMATION: Type II Collagen Fragment with 4Hyp.
<220> FEATURE:
<221> NAME/KEY: MOD_RES
<222> LOCATION: (9)
<223> OTHER INFORMATION: Type II Collagen Fragment with 4Hyp.
<220> FEATURE:
<221> NAME/KEY: MOD_RES
<222> LOCATION: (18)
<223> OTHER INFORMATION: Type II Collagen Fragment with 4Hyp.

<400> SEQUENCE: 67

Gly Pro Xaa Gly Pro Xaa Gly Lys Xaa Gly Asp Asp Gly Glu Ala Gly
  1               5                  10                  15

Lys Xaa Gly Lys Ala
             20

<210> SEQ ID NO 68
<211> LENGTH: 21
<212> TYPE: PRT
<213> ORGANISM: Homo sapiens
<220> FEATURE:
<221> NAME/KEY: MOD_RES
<222> LOCATION: (3)
<223> OTHER INFORMATION: Type II Collagen Fragment with 4Hyp.
<220> FEATURE:
<221> NAME/KEY: MOD_RES
<222> LOCATION: (18)
<223> OTHER INFORMATION: Type II Collagen Fragment with 4Hyp.
<220> FEATURE:
<221> NAME/KEY: MOD_RES
<222> LOCATION: (21)
<223> OTHER INFORMATION: Type II Collagen Fragment with 4Hyp.

<400> SEQUENCE: 68

Gly Pro Xaa Gly Pro Arg Gly Arg Ser Gly Glu Thr Gly Pro Ala Gly
  1               5                  10                  15

Pro Xaa Gly Asn Xaa
             20

<210> SEQ ID NO 69
<211> LENGTH: 22
<212> TYPE: PRT
<213> ORGANISM: Homo sapiens
<220> FEATURE:
<221> NAME/KEY: MOD_RES
<222> LOCATION: (3)
<223> OTHER INFORMATION: Type II Collagen Fragment with 4Hyp.
<220> FEATURE:
<221> NAME/KEY: MOD_RES
<222> LOCATION: (12)
<223> OTHER INFORMATION: Type II Collagen Fragment with 4Hyp.
<220> FEATURE:
<221> NAME/KEY: MOD_RES
<222> LOCATION: (15)
<223> OTHER INFORMATION: Type II Collagen Fragment with 4Hyp.
<220> FEATURE:
<221> NAME/KEY: MOD_RES
<222> LOCATION: (18)
<223> OTHER INFORMATION: Type II Collagen Fragment with 4Hyp.
```

-continued

```
<400> SEQUENCE: 69

Gly Ala Xaa Gly Pro Gln Gly Phe Gln Gly Asn Xaa Gly Glu Xaa Gly
1               5                   10                  15

Glu Xaa Gly Val Ser Tyr
            20
```